(12) United States Patent
Kouzuki et al.

(10) Patent No.: US 7,169,379 B2
(45) Date of Patent: Jan. 30, 2007

(54) COSMETICS

(75) Inventors: Hirokazu Kouzuki, Yokohama (JP);
Morihiro Hirota, Yokohama (JP);
Tomoyuki Inaba, Yokohama (JP);
Haruhiko Inoue, Yokohama (JP);
Hiroshi Itagaki, Yokohama (JP);
Hiroyuki Kakoki, Yokohama (JP);
Takafumi Kurosawa, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 240 days.

(21) Appl. No.: 10/362,171

(22) PCT Filed: Jan. 17, 2002

(86) PCT No.: PCT/JP02/00275

§ 371 (c)(1),
(2), (4) Date: Feb. 21, 2003

(87) PCT Pub. No.: WO02/056852

PCT Pub. Date: Jul. 25, 2002

(65) Prior Publication Data

US 2003/0185772 A1    Oct. 2, 2003

(30) Foreign Application Priority Data

Jan. 19, 2001 (JP) .............................. 2001-011947
Jan. 19, 2001 (JP) .............................. 2001-011948

(51) Int. Cl.
*A61Q 19/00* (2006.01)
*A61Q 17/00* (2006.01)
*A61K 8/00* (2006.01)

(52) U.S. Cl. .................... 424/59; 424/60; 424/400; 424/401

(58) Field of Classification Search ................ 424/59, 424/60, 400, 401
See application file for complete search history.

(56) References Cited

U.S. PATENT DOCUMENTS

| | | | |
|---|---|---|---|
| 4,291,018 A | | 9/1981 | Oeda et al. |
| 4,299,826 A | | 11/1981 | Luedders |
| 4,781,917 A | | 11/1988 | Luebbe et al. |
| 4,869,897 A | * | 9/1989 | Chatterjee et al. ........ 424/47 |
| 5,948,416 A | * | 9/1999 | Wagner et al. ........... 424/401 |
| 6,491,901 B2 | * | 12/2002 | Gers-Barlag et al. ...... 424/59 |

FOREIGN PATENT DOCUMENTS

EP    0928608 A    7/1999
JP    H09-501161 A    2/1997
WO    WO 95/03781 A    2/1995

OTHER PUBLICATIONS

"Comment Regarding Patentability In The Rejection", Japanese Patent Application No. 2002-003635, 1 page.
"Comment Regarding Patentability In The Rejection", Japanese Patent Application No. 2002-003634, 2 pages.
Patent Abstracts of Japan, No. 06-256183, Sep. 13, 1994, and English Abstract.
Patent Abstracts of Japan, No. 06-032710, Feb. 8, 1994, and English Abstract.
Patent Abstracts of Japan, No. 09-291019, Nov. 11, 1997, and English Abstract.
Patent Abstracts of Japan, No. 09-255523, Sep. 30, 1997, and English Abstract.
Patent Abstracts of Japan, No. 09-278625, Oct. 28, 1997, and English Abstract.
Patent Abstracts of Japan, No. 2000-178162, Jun. 27, 2000, and English Abstract.
Patent Abstracts of Japan, No. 06-211628, Aug. 2, 1994, and English Abstract.
Patent Abstracts of Japan, No. 08-183720, Jul. 16, 1996, and English Abstract.
Patent Abstracts of Japan, No. 2000-351712, Dec. 19, 2000 & English Abstract.
Patent Abstracts of Japan, No. 10-095709, Apr. 14, 1998, and English Abstract.
Patent Abstracts of Japan, No. 06-319533, Nov. 24, 1999, and English Abstract.
Patent Abstracts of Japan, No. 2000-256119, Sep. 19, 2000 and English Abstract.
Office Action Rejection from Japanese PTO in Japanese Patent Application No. 2002-3635.
Patent Abstracts of Japan, vol. 0182, No. 51, May 13, 1994 & JP 6 032710 A, Shiseido Co., Ltd.

* cited by examiner

*Primary Examiner*—Shelley A. Dodson
(74) *Attorney, Agent, or Firm*—Townsend & Banta

(57) ABSTRACT

The cosmetic of the present invention is a cosmetic that alleviates skin irritation by blending in polypropylene glycol, a specific polar oil, or polybutylene glycol, as well as an ultraviolet absorbent. The present invention also relates to an agent and a method for alleviating irritation by lipophilic drugs. Since the present invention alleviates skin irritation due to ultraviolet absorbents and lipophilic drugs in cosmetics, any amount of ultraviolet absorbents and lipophilic drugs can be blended in cosmetics, and therefore cosmetics that can fully manifest their effects can be provided. Also, it is possible to prepare a safe sunblock cosmetic with superior ultraviolet protection effects because the ultraviolet absorbent is not absorbed through skin.

6 Claims, 15 Drawing Sheets

COSMETICS

TECHNICAL FIELD

The present invention relates to a cosmetic. The present invention also relates to a skin absorption suppression agent for an ultraviolet absorbent.

The present invention relates to an agent and a method for alleviating irritation by lipophilic drugs blended in an endermic liniment.

BACKGROUND ART

Ultraviolet absorbents have been blended into various cosmetics largely for the purposes of preventing the product from decomposing due to ultraviolet light and of preventing skin damage (sunblock).

Users with sensitive skin sometimes feel irritation from an ultraviolet absorbent in a cosmetic.

Because of this, a method of alleviating this irritation has been sought after strongly.

The inventors searched many common raw materials suitable for a cosmetic base agent, and discovered that polypropylene glycol, specific polar oils, and polybutylene glycol have a very high efficacy in terms of suppressing skin absorption of an ultraviolet absorbent.

And, the inventors discovered that, by blending said polypropylene glycol or specific polar oils or polybutylene glycol in a cosmetic, the skin irritation of sensitive skin can be alleviated without affecting the effect of the ultraviolet absorbent.

The aforementioned polypropylene glycol, specific polar oils, and polybutylene glycol are inexpensive and provide a good sensation during use, rendering them very preferable from the point of view of cosmetic formulation design. Therefore, the aforementioned alkylene glycol and specific polar oils can be used as superior irritation alleviating agents in cosmetics. The significance of the present invention is greater for sunblock cosmetics in particular, because they contain more than a certain amount of an ultraviolet absorbent.

Conventionally, lipophilic drugs are blended into an endermic liniment. Lipophilic drugs have a high affinity to skin and are easily absorbed through skin. Blending lipophilic drugs into an endermic liniment sometimes causes skin irritation on sensitive skin.

A method that employs a urethane compound has been developed in order to alleviate skin irritation due to retinoic acid (JP-T 7-506109 bulletin).

However, since irritation alleviating agents are expensive, the development of low cost irritation alleviating agents has been strongly desired. Also, the development of irritation alleviating agents with good usability and easy formulation design has been strongly desired.

The object of the present invention is to provide an irritation alleviating agent for lipophilic drugs that is inexpensive, has good usability, and allows easy formulation design.

The inventors conducted earnest research and made a new discovery that blending a substance having a high affinity with lipophilic drugs into an endermic liniment suppresses distribution of the lipophilic drugs into the corneum and irritation is alleviated while the effect of the lipophilic drugs on the skin is maintained. This discovery lead to a discovery that polypropylene glycol and polar oils have a particularly high effect of alleviating irritation due to lipophilic drugs.

Said polypropylene glycol and polar oils, when blended into an endermic liniment, exhibit good usability, low cost, and easy formulation design. Polypropylene glycol was found to be particularly superior in alleviating irritation by retinol.

Also, polybutylene glycol was found to have a high effect of alleviating irritation by lipophilic drugs. Polybutylene glycol, when blended into an endermic liniment, exhibits good usability, lowcost, and easy formulation design.

DISCLOSURE OF INVENTION

The present invention is described below. The present invention can provide a cosmetic that has the effect of alleviating irritation by ultraviolet absorbents and lipophilic drugs.

1. A cosmetic comprising an ultraviolet absorbent and polypropylene glycol.
2. A cosmetic comprising an ultraviolet absorbent and at least one of the following polar oils: Diethoxyethyl succinate, diethyl sebacate, diisopropyl sebacate, isononyl isononanoate, dioctyl succinate, trioctanoin, pentaerythrityl tetraoctanoate, and cetyl octanoate.
3. The aforementioned cosmetic wherein said ultraviolet absorbent is octyl methoxycinnamate.
4. The aforementioned cosmetic wherein said cosmetic is a sunblock cosmetic.
5. A skin absorption suppression agent for an ultraviolet absorbent comprising polypropylene glycol.
6. A skin absorption suppression agent for an ultraviolet absorbent comprising at least one of the following polar oils.

Diethoxyethyl succinate, diethyl sebacate, diisopropyl sebacate, isononyl isononanoate, dioctyl succinate, trioctanoin, pentaerythrityl tetraoctanoate, and cetyl octanoate.

7. A cosmetic comprising an ultraviolet absorbent and polybutylene glycol.
8. The aforementioned cosmetic wherein said ultraviolet absorbent is octyl methoxycinnamate.
9. The aforementioned cosmetic wherein said cosmetic is a sunblock cosmetic.
10. A skin absorption suppression agent for an ultraviolet absorbent comprising polybutylene glycol.
11. An irritation alleviating agent for lipophilic drugs comprising polypropylene glycol.
12. An irritation alleviating agent for lipophilic drugs comprising polar oil.
13. A method of alleviating irritation by lipophilic drugs using said irritation alleviating agent.
14. An irritation alleviating endermic liniment containing said irritation alleviating agent.
15. An endermic liniment comprising retinol and polypropylene glycol having a number average molecular weight of 1,500–2,500.
16. An irritation alleviating agent for lipophilic drugs comprising polybutylene glycol.
17. A method of alleviating irritation by lipophilic drugs using said irritation alleviating agent.
18. An irritation alleviating endermic liniment containing said irritation alleviating agent.

BEST MODE FOR CARRYING OUT THE INVENTION

Figure 1:
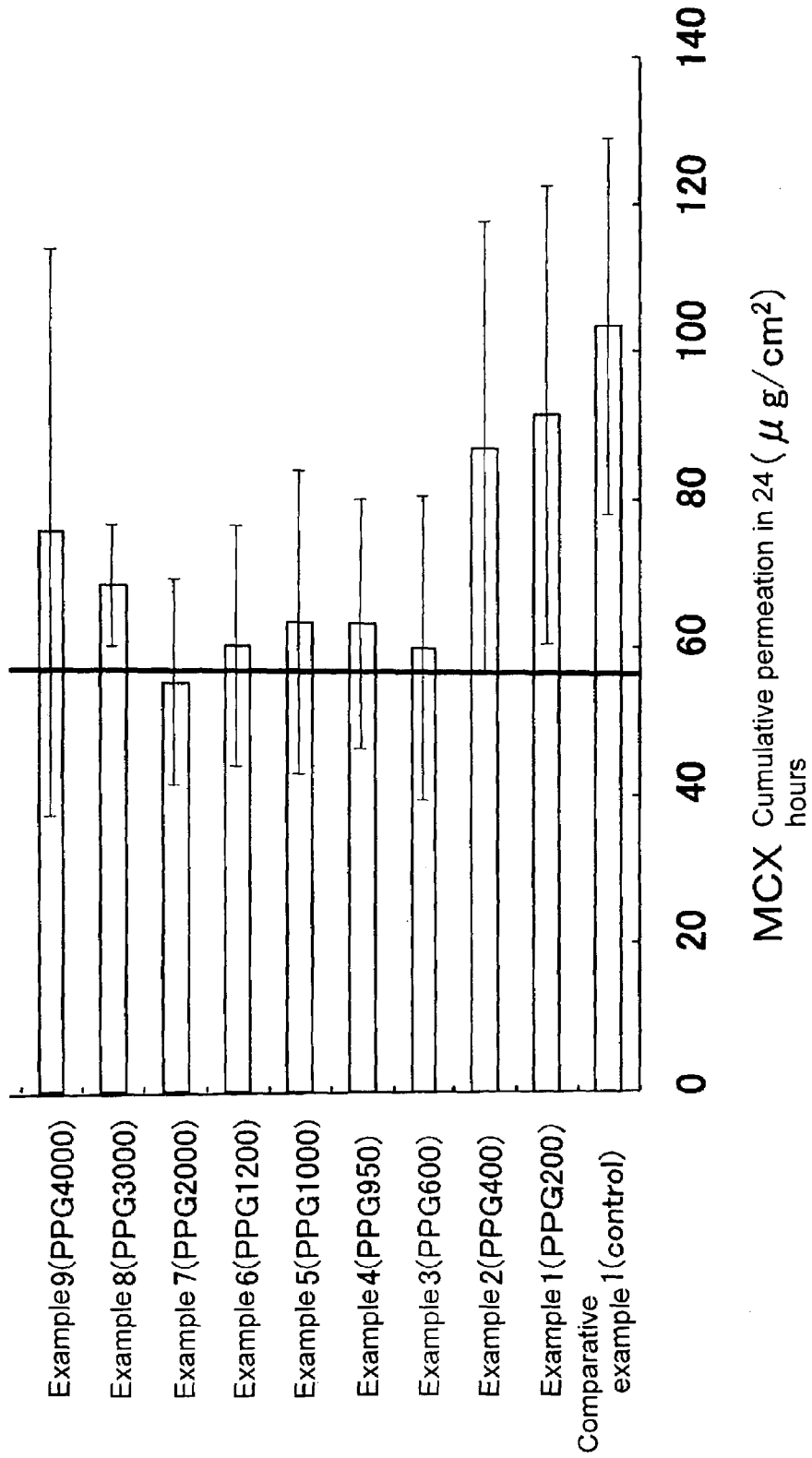
FIG. 1 is a graph showing the cumulative permeation of an ultraviolet absorbent in 24 hours.

The present invention is described below.

(1) Invention Described in Claims 1–10

Examples of ultraviolet absorbents used in the present invention is as follows:

Octyl methoxycinnamate (trade name: Parsol MCX)
t-Butyl methoxybenzoyl methane (trade name: Parsol 1789)
Methylbis (trimethylsiloxy) silyl isopentyl trimethoxycinnamate (trade name: Sun shelter SP)
2-Ethylhexyl paradimethylaminobenzoate (trade name: Escalol 507D)
Methyl paradimethylaminobenzoate (trade name: Escalol 506)

Examples of polypropylene glycol (PPG) used in the present invention is as follows: PPG200, PPG400, PPG600, PPG950, PPG1000, PPG1200, PPG2000, PPG3000, and PPG4000.

Any commercially available polypropylene glycol can be selected for use.

Those with a number average molecular weight of 500–2,500 have a superior skin absorption suppression effect.

The number average molecular weight can be determined by a method mentioned in page 942 in Cosmetic Material Standard, the second edition explanatory note I (1984 Yakuji Nippo-sha).

The polar oil used in the present invention is an oil having a polar structure in its molecule, examples of which is as follows:

Diethoxyethyl succinate, diethyl sebacate, diisopropyl sebacate, isononyl isononanoate, dioctyl succinate, trioctanoin, pentaerythrityl tetraoctanoate, and cetyl octanoate.

Examples of polybutylene glycol (PBG) used in the present invention is as follows: PBG700, PBG1000, PBG2000, and PBG4800.

Any commercially available polybutylene glycol can be selected for use.

Those with a number average molecular weight higher than 500 have a superior skin absorption suppression effect.

The number average molecular weight can be determined by a method mentioned in page 942 in Cosmetic Material Standard, the second edition explanatory note I (1984 Yakuji Nippo-sha).

The blend ratio of an ultraviolet absorbent, when used for the cosmetics stability against decomposition, is usually 0.01–1.0 mass % of the total amount of the cosmetic.

When the ultraviolet absorbent is used to protect skin from ultraviolet light, the blend ratio is usually 1.0–5.0 mass %.

When used specifically for a sunblock cosmetic, the blend ratio is usually 5.0–15.0 mass %.

When the blend ratio of the ultraviolet absorbent is 5.0 mass % or higher, the possibility of skin irritation of sensitive skin becomes high and the irritation alleviating effect increases.

The blend ratio of the polypropylene glycol is 0.1–20.0 mass %, preferably 1.0–10.0 mass %, of the total amount of the cosmetic.

The blend ratio of the polar oil is 0.1–20.0 mass %, preferably 1.0–10.0 mass %, of the total amount of the cosmetic.

The blend ratio of the polybutylene glycol is 0.1–20.0 mass %, preferably 1.0–10.0 mass %, of the total amount of the cosmetic.

In the present invention, octyl methoxycinnamate (trade name: Parsol MCX) has a particularly high effect of alleviating irritation.

The blend ratio of the polypropylene glycol is preferably 10–50 mass % of the octyl methoxycinnamate; for example, the skin absorption suppression effect of the octyl methoxycinnamate is high when the blend ratio of the polypropylene glycol is 2–4 mass % while the blend ratio of the methoxy cinnamate is 7.5 mass %.

The blend ratio of the polar oil is preferably 30–70 mass % of the octyl methoxycinnamate; for example, the skin absorption suppression effect of the octyl methoxycinnamate is high when the blend ratio of the polar oil is 3–5 mass % while the blend ratio of the methoxy cinnamate is 7.5 mass %.

The blend ratio of the polybutylene glycol is preferably 10–50 mass % of the octyl methoxycinnamate; for example, the skin absorption suppression effect of the octyl methoxycinnamate is high when the blend ratio of the polybutylene glycol is 1–4 mass % while the blend ratio of the methoxy cinnamate is 7.5 mass %.

The formulation of the cosmetic is not limited.

Examples include liquids, emulsions, gels, pastes, and creams.

The product form of the sunscreen cosmetic is not limited either. A sunblock cosmetic stands for a cosmetic that protects skin from ultraviolet light.

The cosmetic of the present invention is prepared with a conventional method according to the target formulation by blending the aforementioned essential ingredients with the ingredients of the cosmetics (such as humectants, oils, surfactants, thickeners, sequestering agents, ultraviolet inhibitors, drugs, colors, and perfumes).

(2) Invention Described in Claims 11–18

Examples of polypropylene glycol used in the present invention is as follows: PPG200, PPG400, PPG600, PPG950, PPG1000, PPG1200, PPG2000, PPG3000, and PPG4000.

Any commercially available polypropylene glycol can be selected for use.

Those with a number average molecular weight of 400–2,500 have a superior irritation alleviating effect.

Those with a number average molecular weight of 1,500–2,000 are particularly superior.

The number average molecular weight can be determined by, for example, estimating the terminal OH of the polypropylene glycol. This is the same as a method of measuring the average molecular weight of polyethylene glycol mentioned in page 942 in Cosmetic Material Standard, the second edition explanatory note I (1984 Yakuji Nippo-sha).

The polar oil used for the irritation alleviating agent in the present invention is an oil having a polar structure in its molecule. Preferable polar oils is as follows:

Diethoxyethyl succinate, diethyl sebacate, diisopropyl sebacate, isononyl isononanoate, dioctyl succinate, trioctanoin, pentaerythrityl tetraoctanoate, and cetyl octanoate.

Examples of polybutylene glycol (PBG) used for the irritation alleviating agent in the present invention is as follows: PBG700, PBG1000, PBG2000, and PBG4800.

Any commercially available polybutylene glycol can be selected for use.

Those with a number average molecular weight higher than 500 have a superior irritation alleviating effect.

The number average molecular weight can be determined by a method mentioned in page 942 in Cosmetic Material Standard, the second edition explanatory note I (1984 Yakuji Nippo-sha).

In the present invention, a lipophilic drug is a lipophilic active ingredient usually blended in an endermic liniment (cosmetics, quasi-drugs, and medical drugs).

A lipophilic drug is an active ingredient that is soluble in oil and is easily absorbed through skin.

Therefore, when it is blended into an endermic liniment, skin irritation may occur on sensitive skin.

Examples of the lipophilic drugs whose irritating effects are alleviated in the present invention include the following:

(1) Retinol and its Derivatives

There are the all-trans form or the cis form of retinol (or vitamin A).

Examples of retinol derivatives include retinol acetate (or vitamin A acetate) and retinol palmitate (or vitamin A palmitate).

(2) Ultraviolet Absorbent

Examples include benzoic acid ultraviolet absorbents (such as paraaminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid ultraviolet absorbents (such as homomentyl-N-acetyl anthranilate) ; salicylic acid ultraviolet absorbents (such as amyl salicylate, menthyl salicylate, homomentyl salicylate, octyl salicylate, phenyl salicylate, benzyl salicylate, and p-isopropanol phenyl salicylate); cinnamic acid ultraviolet absorbent (such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethyl hexanoyl-dipara methoxycinnamate); benzophenone ultraviolet absorbents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d, l-camphor, 3-benzylidene-d, l-camphor; 2-phenyl-5-methyl benzoxazole; 2,2'-hydroxy-5-methylphenyl benzotriazol; 2-(2'-hydroxy-5'-t-octylphenyl)benzotriazol; 2-(2'-hydroxy-5'-methylphenylbenzotriazol;) dibenzaladine; dianisoylmethane; 4-methoxy-4'-t-butyldibenzoylmethane; and 5-(3,3-dimethyl-2-norbornylidene)-3-pentane-2-one.

The present invention is used preferably for the following ultraviolet absorbents that have caused irritation.

Octyl methoxycinnamate (trade name: Parsol MCX)

t-Butyl methoxybenzoyl methane (trade name: Parsol 1789)

Methylbis(trimethlylsiloxy)silylisopentyl-trimethoxycinnamate (trade name: Sun shelter SP)

2-Ethylhexylparadimethylaminobenzoate (trade name: Escalol 507D)

Methylparadimethylaminobenzoate (trade name: Escalol 506)

(3) Preservatives

Paraben, methylparaben, and phenoxyethanol.

The irritation alleviating endermic liniment of the present invention contains the aforementioned irritation alleviating agent as well as the lipophilic drug and the skin irritation by the lipophilic drug is alleviated.

The blend ratio of the irritation alleviating agent is 0.1–20.0 mass %, preferably 1.0–10.0 mass %, of the total amount of the endermic liniment.

The blend ratio of the lipophilic drug is determined based on the type of the drug.

In the case of retinol the blend ratio is 0.01–1.0 mass %, preferably 0.05–0.1 mass %, of the total amount of the endermic liniment, whereas in the case of an ultraviolet absorbent the blend ratio is 0.1–20.0 mass %, preferably 1.0–10.0 mass %, of the total amount of the endermic liniment.

Polypropylene glycol is particularly superior for alleviating irritation by retinol.

The blend ratio of the polypropylene glycol in this case is determined based on the blend ratio of retinol.

Usually, a blend ratio of 1 mass % of the total amount of the endermic liniment achieves the irritation alleviating effect. 3 mass % is preferable.

As for the molecular weight of the polypropylene glycol, 500–2,500 is preferable; 1,500–2,500 is particularly preferable.

The blend ratio between polypropylene glycol and retinol (PPG/retinol) is preferably 2–100, more preferably 10–50.

The formulation of the irritation alleviating endermic liniment is not limited.

Examples include liquids, gels, pastes, and creams.

The irritation alleviating endermic liniment is prepared with a conventional method according to the target formulation by blending the aforementioned essential ingredients with the ingredients of the endermic liniment (such as humectants, oils, surfactants, thickeners, sequestering agents, ultraviolet inhibitors, drugs, colors, and perfumes).

EXAMPLES

The present invention is described below by referring to Examples. The blend ratios are in mass % units.

For each cosmetic, the following tests were conducted to confirm the effect of the present invention.

"Skin Absorption Test of the Lipophilic Drug"

Test Method:
1. Commercially available lab-skin (hairless mouse) was attached to a Franz-type diffusion cell.
2. A sample solution containing a lipophilic drug was injected into the donor side of a diffusion cell.
3. A phosphate buffer (pH 7.4) containing 0.1% sodium azide and 0.5–6% polyoxyethylene (20) oleyl ether was injected into the receiver side of the diffusion cell.
4. The receiver side was stirred with a magnetic stirrer and a thermostatic bath was used to maintain the temperature at 37° C.
5. Sampling was done periodically from the receiver side.
6. An assay of the sample was done by using HPLC.

Evaluation Method:
Skin absorption was evaluated based on the cumulative amount of the sample permeated into the receiver side.

"Continuous Skin Irritation Test"

Test Method:
1. 0.05 ml of a sample solution containing a lipophilic drug was applied on a 2×2 cm area of the back of a marmot (first application).
2. 24 hours later, the second application was done.
3. Again, 24 hours later, the third application was done.

Evaluation Method:
Before the second application, before the third application, and 24 hours after the third application, skin reactions such as erythema and edema was observed by naked eye. Evaluation was conducted based on the following criteria, and the average of the three scores was used as the skin reaction score.

Evaluation Criteria of the Skin Reaction

| Degree of the skin reaction | Score |
|---|---|
| No erythema was observed. | 0 |
| Erythema was barely observable. | 1 |
| Erythema was prominently observable. | 2 |
| Severe erythema, little edema, and scabs were observable. | 3 |

Edema and Scabs were Prominently Observable.

(1) Invention Described in Claims 1–10

1. A cosmetic comprising an ultraviolet absorbent and polypropylene glycol (PPG).

Examples 1–9

A sunscreen with a recipe listed in the following Table 1 was prepared with a conventional method.

A skin absorption test was conducted.

As for the polypropylene glycol, PPG200–4000 were used.

TABLE 1

Blend ratios are in mass % units.

| Raw material name | Comparative example 1 control | Example 1 PPG200 | Example 2 PPG400 | Example 3 PPG600 | Example 4 PPG950 | Example 5 PPG1000 | Example 6 PPG1200 | Example 7 PPG2000 | Example 8 PPG3000 | Example 9 PPG4000 |
|---|---|---|---|---|---|---|---|---|---|---|
| Ion-exchange water | Balance | Balance | Balance | Balance | Balance | Balance | Balance | Balance | Balance | Balance |
| PPG-200 | — | 3 | — | — | — | — | — | — | — | — |
| PPG-400 | — | — | 3 | — | — | — | — | — | — | — |
| PPG-600 | — | — | — | 3 | — | — | — | — | — | — |
| PPG-950 | — | — | — | — | 3 | — | — | — | — | — |
| PPG-1000 | — | — | — | — | — | 3 | — | — | — | — |
| PPG-1200 | — | — | — | — | — | — | 3 | — | — | — |
| PPG-2000 | — | — | — | — | — | — | — | 3 | — | — |
| PPG-3000 | — | — | — | — | — | — | — | — | 3 | — |
| PPG-4000 | — | — | — | — | — | — | — | — | — | 3 |
| 1,3-butylene glycol | 5 | 5 | 5 | 5 | 5 | 5 | 5 | 5 | 5 | 5 |
| POE/methyl polysiloxane copolymer | 2 | 2 | 2 | 2 | 2 | 2 | 2 | 2 | 2 | 2 |
| Clay mineral (Hectorite) | 0.5 | 0.5 | 0.5 | 0.5 | 0.5 | 0.5 | 0.5 | 0.5 | 0.5 | 0.5 |
| Decamethyl-cyclopentasiloxane | 30 | 30 | 30 | 30 | 30 | 30 | 30 | 30 | 30 | 30 |
| Trimethylsiloxysilicic acid-Decamethyl-cyclopentasiloxane solution | 5 | 5 | 5 | 5 | 5 | 5 | 5 | 5 | 5 | 5 |
| Methyl polysiloxane | 5 | 5 | 5 | 5 | 5 | 5 | 5 | 5 | 5 | 5 |
| Octyl methoxycinnamate | 7.5 | 7.5 | 7.5 | 7.5 | 7.5 | 7.5 | 7.5 | 7.5 | 7.5 | 7.5 |
| Fine particle zinc oxide | 20 | 20 | 20 | 20 | 20 | 20 | 20 | 20 | 20 | 20 |
| Methyl polymethacrylate | 4 | 4 | 4 | 4 | 4 | 4 | 4 | 4 | 4 | 4 |
| EDTA-3Na.2H$_2$O | 0.05 | 0.05 | 0.05 | 0.05 | 0.05 | 0.05 | 0.05 | 0.05 | 0.05 | 0.05 |

TABLE 1-continued

Blend ratios are in mass % units.

| Raw material name | Comparative example 1 control | Example 1 PPG200 | Example 2 PPG400 | Example 3 PPG600 | Example 4 PPG950 | Example 5 PPG1000 | Example 6 PPG1200 | Example 7 PPG2000 | Example 8 PPG3000 | Example 9 PPG4000 |
|---|---|---|---|---|---|---|---|---|---|---|
| Methylparaben | Appropriate amount | Appropriate amount | Appropriate amount | Appropriate amount | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount | Appropriate amount | Appropriate amount | Appropriate amount | Appropriate amount |
| Total | 100 | 100 | 100 | 100 | 100 | 100 | 100 | 100 | 100 | 100 |

Example 10

This is similar to Example 8 except for the fact that the blend ratio of PPG3000 was changed to 1 mass %.

Example 11

This is similar to Example 8 except for the fact that the blend ratio of PPG3000 was changed to 7.5 mass %.
A skin absorption test was conducted.

Example 12

This is similar to Example 5 except for the fact that the blend ratio of PPG1000 was changed to 1 mass %.

Example 13

This is similar to Example 5 except for the fact that the blend ratio of PPG1000 was changed to 2 mass %.
A continuous skin irritation test was conducted.

2. A cosmetic comprising an ultraviolet absorbent and polar oil.

Examples 14–21

A sunscreen with the following recipe was prepared with a conventional method.
A skin absorption test was conducted.

TABLE 2

Blend ratios are in mass % units.

| Raw meterial name | Comparative example 2 control | Example 14 Cetyl octanoate | Example 15 Trioctanoin | Example 16 Pentaerythrityl tetraoctanoate | Example 17 Diisopropyl sebacate | Example 18 Isononyl isononanoate | Example 19 Isooctyl succinate | Example 20 Diethyl sebacate | Example 21 Diethoxyethyl succinate | Comparative example 3 Squalane (nonpolar) |
|---|---|---|---|---|---|---|---|---|---|---|
| Purified water | Balance | Balance | Balance | Balance | Balance | Balance | Balance | Balance | Balance | Balance |
| 1,3-butylene glycol | 5 | 5 | 5 | 5 | 5 | 5 | 5 | 5 | 5 | 5 |
| POE/methyl polysiloxane copolymer | 2 | 2 | 2 | 2 | 2 | 2 | 2 | 2 | 2 | 2 |
| Clay mineral (Hectorite) | 0.5 | 0.5 | 0.5 | 0.5 | 0.5 | 0.5 | 0.5 | 0.5 | 0.5 | 0.5 |
| Trimethylsiloxysilicic acid-Decamethylcyclopentasiloxane solution | 5 | 5 | 5 | 5 | 5 | 5 | 5 | 5 | 5 | 5 |
| Decamethylcyclopentasiloxane | 30 | 30 | 30 | 30 | 30 | 30 | 30 | 30 | 30 | 30 |
| Methyl polysiloxane | 4 | — | — | — | — | — | — | — | — | — |
| Cetyl octanoate | — | 4 | — | — | — | — | — | — | — | — |
| Trioctanoin | — | — | 4 | — | — | — | — | — | — | — |
| Pentaerythrityl tetraoctanoate | — | — | — | 4 | — | — | — | — | — | — |
| Diisopropyl sebacate | — | — | — | — | 4 | — | — | — | — | — |
| Isononyl isononanoate | — | — | — | — | — | 4 | — | — | — | — |
| Isooctyl succinate | — | — | — | — | — | — | 4 | — | — | — |
| Diethyl sebacate | — | — | — | — | — | — | — | 4 | — | — |
| Diethoxyethyl succinate | — | — | — | — | — | — | — | — | 4 | — |
| Squalane | — | — | — | — | — | — | — | — | — | 4 |

TABLE 2-continued

Blend ratios are in mass % units.

| Raw meterial name | Comparative example 2 control | Example 14 Cetyl octanoate | Example 15 Trioctanoin | Example 16 Pentaerythrityl tetraoctanoate | Example 17 Diisopropyl sebacate | Example 18 Isononyl isononanoate | Example 19 Isooctyl succinate | Example 20 Diethyl sebacate | Example 21 Di-ethoxyethyl succinate | Comparative example 3 Squalane (nonpolar) |
|---|---|---|---|---|---|---|---|---|---|---|
| Octyl methoxycinnamate | 7.5 | 7.5 | 7.5 | 7.5 | 7.5 | 7.5 | 7.5 | 7.5 | 7.5 | 7.5 |
| Zinc oxide treated with dextrin palmitate | 20 | 20 | 20 | 20 | 20 | 20 | 62 | 20 | 20 | 20 |
| Methyl polymethacrylate | 5 | 5 | 5 | 5 | 5 | 5 | 5 | 5 | 5 | 5 |
| EDTA.3Na.2H$_2$O | 0.05 | 0.05 | 0.05 | 0.05 | 0.05 | 0.05 | 0.05 | 0.05 | 0.05 | 0.05 |
| Methylparaben | Appropriate amount | Appropriate amount | Appropriate amount | Appropriate amount | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount | Appropriate amount | Appropriate amount | Appropriate amount | Appropriate amount |
| | 100 | 100 | 100 | 100 | 100 | 100 | 100 | 100 | 100 | 100 |

"Description of FIG. 1"

Compared with Comparative example 1 (control), the cosmetics of Examples 1–9 had a smaller cumulative permeation in 24 hours, which confirms the skin absorption suppression effect.

In particular, the results of Examples 3–7 indicate that polypropylene glycol having an average molecular weight of 600–2,000 has a superior skin absorption suppression effect. Example 7 with an average molecular weight of 2,000 is particularly superior; therefore, PPG with an average molecular weight of 1,500–2,500 is expected to manifest a particularly superior skin absorption suppression effect.

Figure 2:
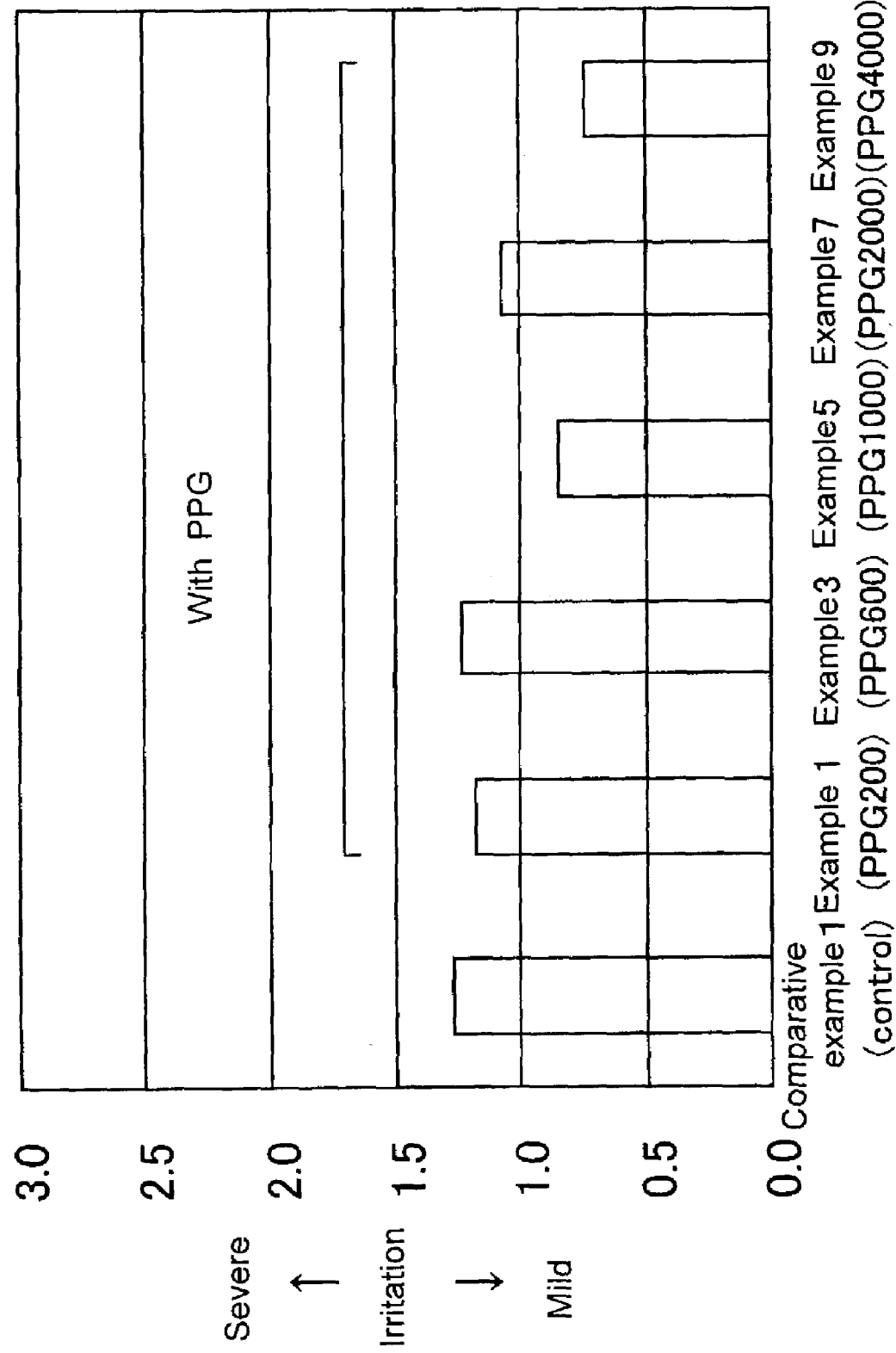
FIG. 2 is a graph showing continuous skin irritation test results of an ultraviolet absorbent.

"Description of FIG. 2"

The cosmetics of Examples 1, 3, 5, 7, and 9 are confirmed to have less skin irritation compared with Comparative example 1 (control).

Figure 3:
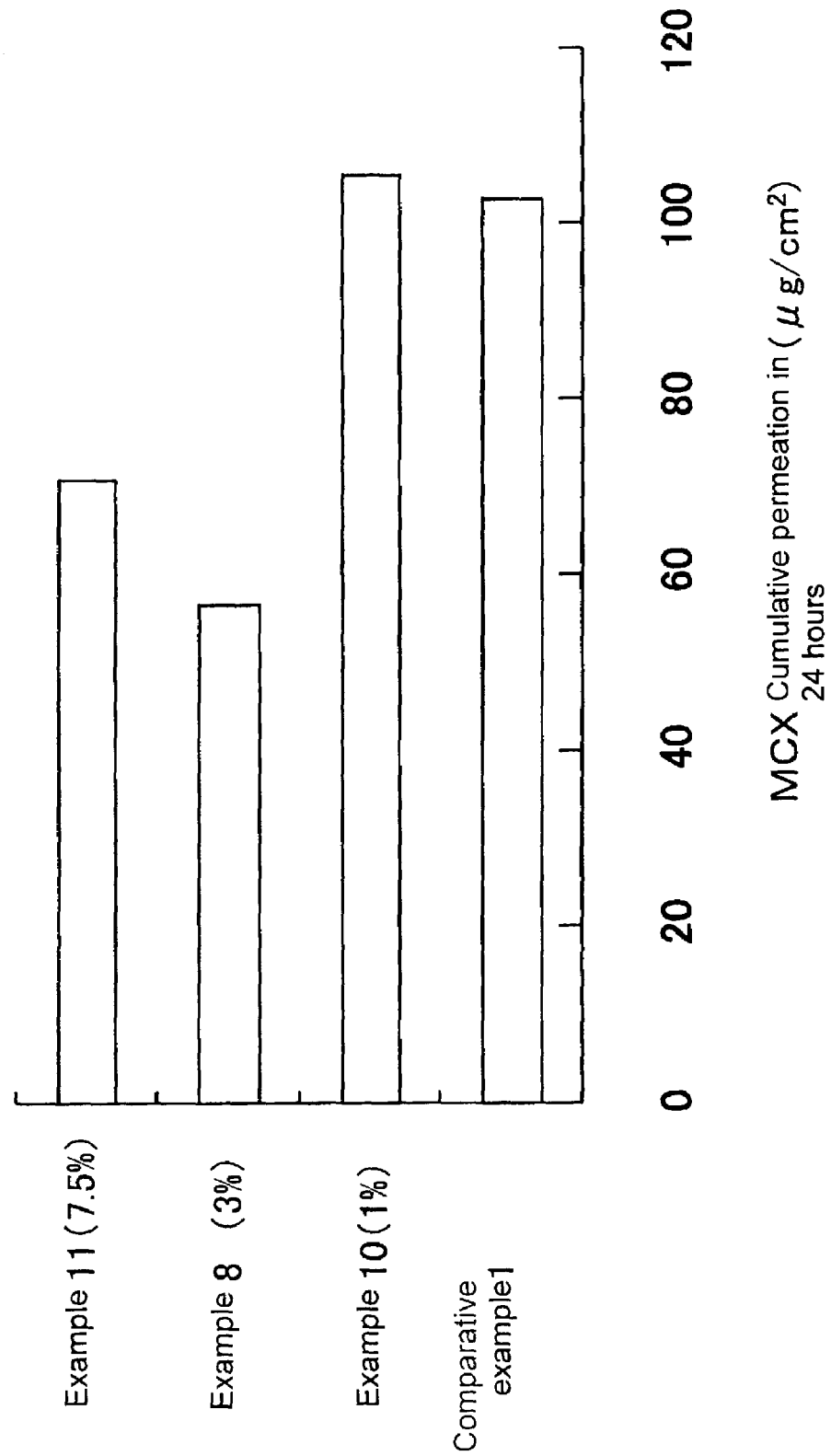
FIG. 3 is a graph showing the cumulative permeation of an ultraviolet absorbent in 24 hours.

"Description of FIG. 3"

Examples 8, 10, and 11 were investigated for the relationship between the blend ratio of PPG and the skin absorption suppression effect.

A prominent skin absorption suppression effect is observed when the blend ratio of PPG is 3 mass %.

Figure 4:
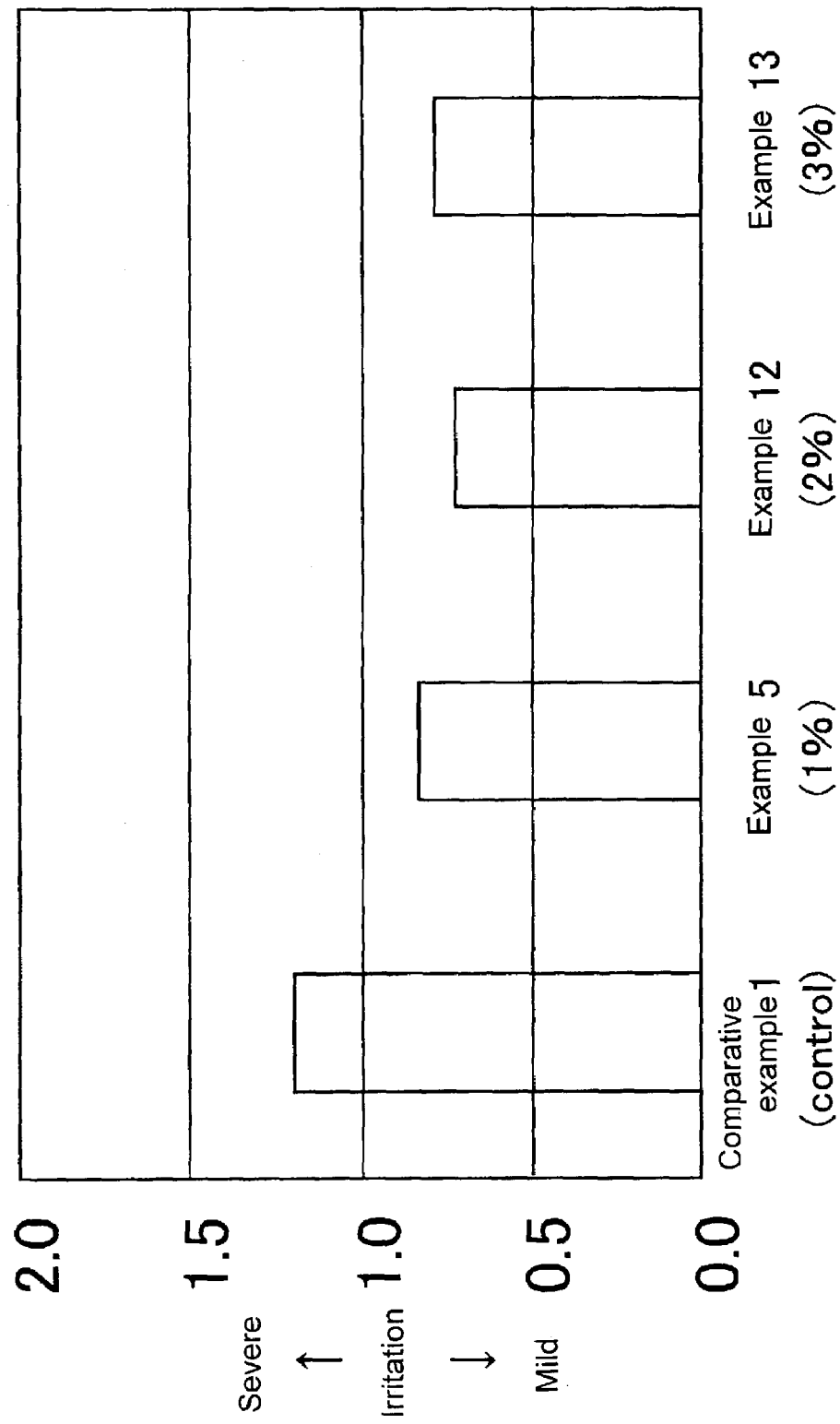
FIG. 4 is a graph showing the continuous skin irritation test results of an ultraviolet absorbent.

"Description of FIG. 4"

Examples 5, 12, and 13 were investigated for the relationship between the blend ratio of PPG and the continuous skin irritation suppression effect.

A prominent skin irritation suppression effect is observed when the blend ratio of PPG is 1–3 mass %.

Figure 5:
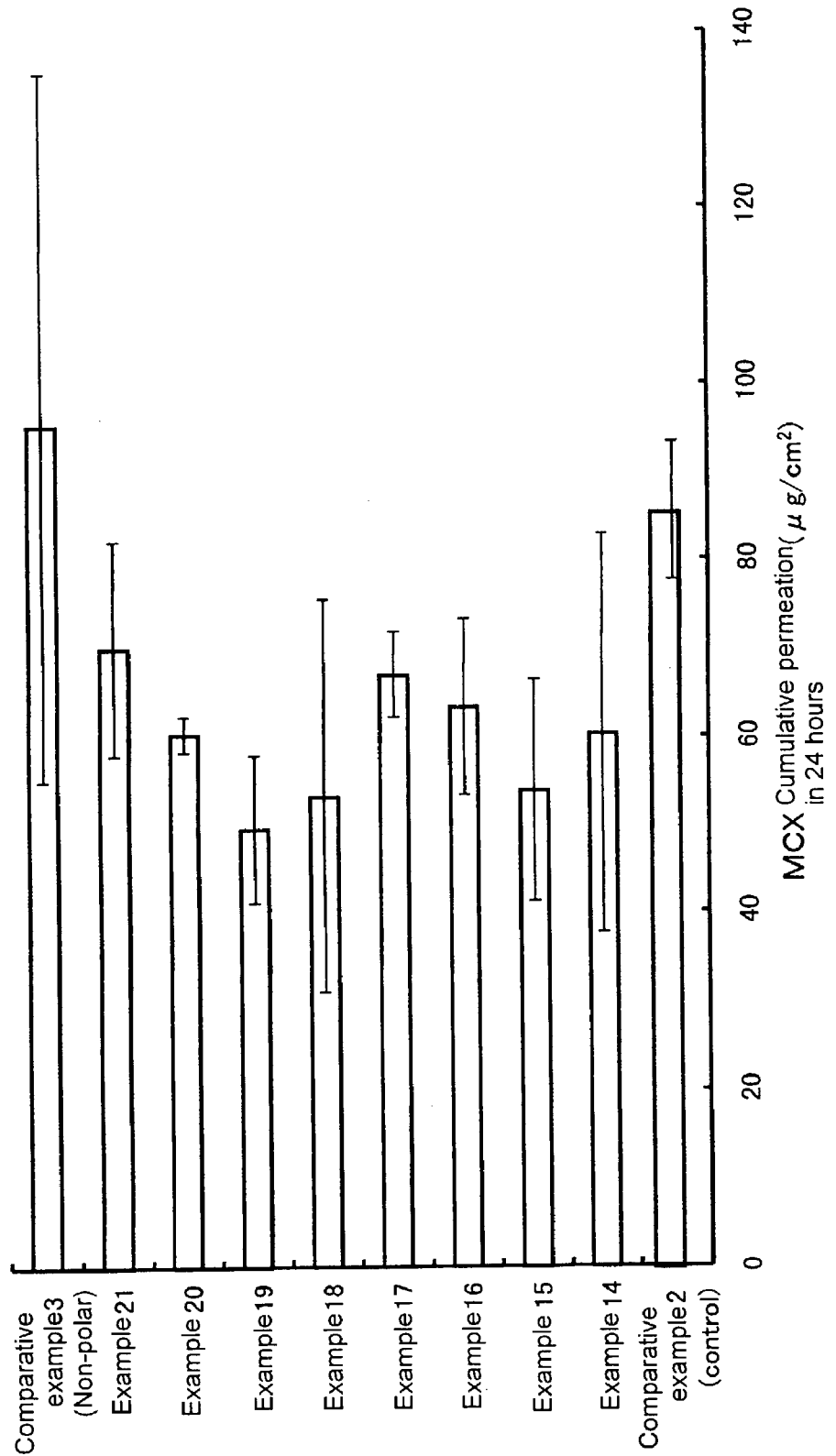
FIG. 5 is a graph showing the cumulative permeation of an ultraviolet absorbent in 24 hours.

"Description of FIG. 5"

The Cosmetics of Examples 14–21 have a Superior Skin Absorption Suppression Effect Examples 15, 18, and 19 (trioctanoin, isononyl isononanoate, and isooctyl succinate) have a particularly superior effect.

Examples of the present invention are listed below.

Each of them suppresses skin absorption of an ultraviolet absorbent and has an irritation alleviating effect.

Example 22

Sunscreen

| | |
|---|---|
| Octyl methoxycinnamate | 7.5 |
| Polypropylene glycol 1000 | 2.0 |
| t-Butyl methoxy dibenzoyl-methane | 0.1 |
| Titanium dioxide | 5.0 |
| Decamethylcyclopentasiloxane | 30.0 |
| POE/methylpolysiloxane copolymer | 3.0 |
| Organo-modified montmorillonite | 0.8 |
| 1,3-Butylene glycol | 5.0 |
| Arbutin | 5.0 |
| Preservative | Appropriate amount |
| Perfume | Appropriate amount |
| Purified water | Balance |

Example 23

Cream

A

| | |
|---|---|
| Squalane | 6.0 |
| Cetyl octanoate | 4.0 |
| Petrolatum | 5.0 |
| Stearyl alcohol | 3.0 |
| Stearic acid | 3.0 |
| Glyceryl monostearate | 3.0 |
| Ethyl polyacrylate | 1.0 |
| t-Butyl methoxybenzoyl methane | 7.5 |
| Polyamide resin powder | 5.0 |
| Ethanol | 40.0 |
| Preservative | Appropriate amount |
| Perfume | Appropriate amount |

B

| | |
|---|---|
| 1,3-Butylene glycol | 7.0 |
| Trisodium edetate | 0.05 |
| Cationic thickener | 3.0 |
| Lactic acid | 0.6 |
| Purified water | Balance |

(Preparation Method) The ingredients in A were heated and melted, to which B was added while stirring. A homogenizer was used to make the emulsion particles finer, followed by rapid cooling with stirring to obtain a cream.

Example 24

Lotion

A

| | |
|---|---|
| Octylmethoxycinnamate | 2.0 |
| Tetrapentaerythrityloctanoate | 1.0 |
| Polyoxyethylene (20) oleyl alcohol ether | 0.5 |
| Ethanol | 60.0 |
| Perfume | Appropriate amount |
| Preservative | Appropriate amount |

B

| | |
|---|---|
| Sorbitol | 4.0 |
| Dipropylene glycol | 6.0 |
| Polyethylene glycol 1500 | 5.0 |
| Lactic acid | 0.1 |
| Citric acid | 0.1 |
| Sodium citrate | 0.05 |
| Hydroxy methoxy benzophenone sodium sulfonate | Appropriate amount |
| Trisodium edetate | Appropriate amount |
| Purified water | Balance |

(Preparation Method) B was prepared. Separately, in the ethanol, the rest of the ingredients of A were dissolved to prepare A, which was added to B and dissolved and filtered to obtain a lotion.

Example 25

Emulsion

A

| | |
|---|---|
| Stearic acid | 2.0 |
| Cetyl alcohol | 0.5 |
| Liquid petrolatum | 10.0 |
| Polyoxyethylene (10) oleate | 1.0 |
| Sorbitan trioleate | 1.0 |
| Octylmethoxycinnamate | 3.0 |
| Tetrapentaerythrityl octanoate | 1.5 |
| Isopropyl myristate | 2.0 |
| Silica | 3.0 |
| Preservative | Appropriate amount |
| Perfume | Appropriate amount |

B

| | |
|---|---|
| Dipropylene glycol | 5.0 |
| Polyethylene glycol 1500 | 5.0 |
| Triethanolamine | 1.0 |
| Hectorite | 1.0 |
| Citric acid | 0.2 |
| Ethanol | 55.0 |
| Purified water | Balance |

(Preparation method) B was prepared and the temperature was kept at 70° C. The ingredients in A were mixed, heated and melted and the temperature was kept at 70° C. A was added to B, followed by rapid cooling while a homogenizer was used for emulsification and stirring to obtain an emulsion.

Example 26

Sunblock Hair Gel

A

| | |
|---|---|
| Carbopol 940 | 0.6 |

B

| | |
|---|---|
| Purified water | 68.0 |

C

| | |
|---|---|
| Triethanolamine | 0.1 |

D

| | |
|---|---|
| Ethanol | 14.0 |
| Octylmethoxycinnamate | 7.5 |
| Cetyl octanoate | 4.0 |
| Methoxyethyl acrylate/hydroxyethyl acrylate/butyl acrylate copolymer | 1.0 |
| Polyethylene glycol | 1.0 |
| Dimethicone copolymer | 4.0 |
| Methylparaben | 0.25 |
| Propylparaben | 0.05 |
| Perfume | Appropriate amount |

(Preparation method) A was dissolved in B while stirring, to which C was added and dispersed with a disperser, to which D was added and stirred to obtain the target hair gel.

Example 27

Sunblock Emulsified Foundation

A

| | |
|---|---|
| Purified water | 52.0 |
| 1,3-butylene glycol | 5.0 |
| Ethanol | 7.0 |

B

| | |
|---|---|
| Talc | 7.0 |
| Titanium dioxide | 10.0 |
| Zinc oxide | 2.0 |
| Silicic acid anhydride | 2.0 |
| Nylon powder | 4.0 |
| Color pigment | 2.0 |

C

| | |
|---|---|
| Paramethoxycinnamate | 15.0 |
| Tetrapentaerythrityl octanoate | 4.0 |
| Octamethylcyclotetrasiloxane | 10.0 |
| Pentaerythritol rosinate | 1.5 |
| Neopentyl glycol diisooctanoate | 5.0 |
| Glycerin triisooctanoate | 2.0 |
| Polyoxyethylene modified dimethylpolysiloxane | 1.5 |
| Trimethylsiloxy silicic acid resin | 5.0 |

(Preparation method) After stirring A, thoroughly mixed and crushed B was added, follow by a homogenizer treatment. C was dissolved and added to this, followed by a homogenizer treatment to obtain a sunblock emulsified foundation.

Next, the skin absorption test and the continuous skin irritation test were conducted for polybutylene glycol (PBG) in the same manner as described above.

Example 28 is a cosmetic similar to Example 1 except for the fact that 2 mass % PBG4800, instead of PPG200, was blended in.

Example 29 is a cosmetic similar to Example 1 except for the fact that 2 mass% PBG2000, instead of PPG200, was blended in.

Example 30 is a cosmetic similar to Example 1 except for the fact that 2 mass % PBG1000, instead of PPG200, was blended in.

Figure 6:
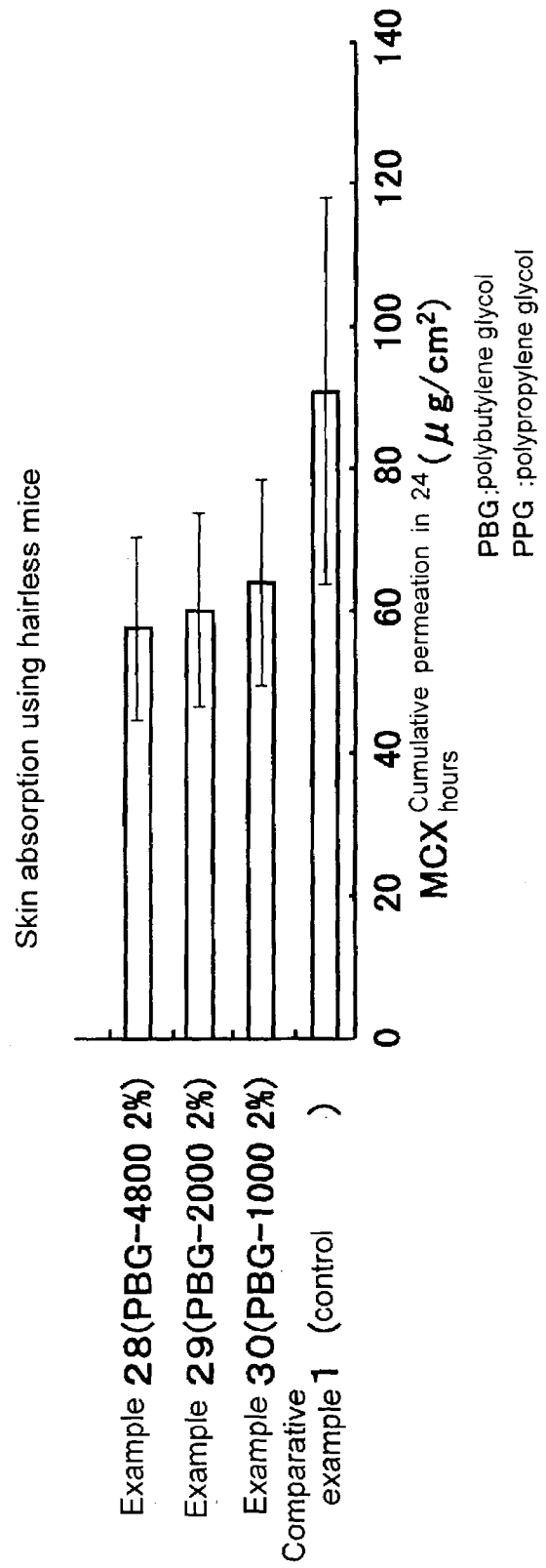
FIG. 6 is a graph showing the cumulative permeation of an ultraviolet absorbent in 24 hours.
Figure 7:
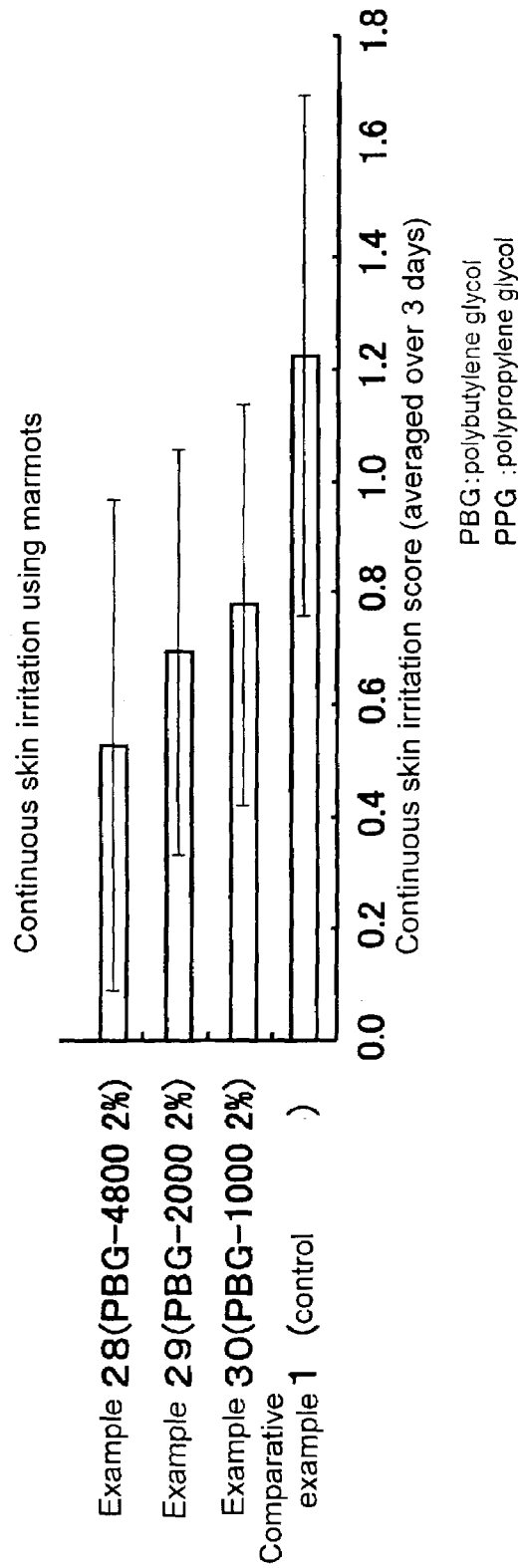
FIG. 7 is a graph showing the continuous skin irritation test results of an ultraviolet absorbent.

The results of the skin absorption test and the continuous skin irritation test for the aforementioned cosmetics of Examples 28–30 are shown in FIGS. 6 and 7.

"Description of FIG. 6"

Using the cosmetics of Examples 28–30, the skin absorption test of octyl methoxycinnamate (MCX) was conducted with the aforementioned method using hairless mouse skin.

The results for Comparative example 1 are also shown in FIG. 7.

The cosmetics of Examples 28–30 have a superior skin absorption suppression effect compared with Comparative example 1 (control).

"Description of FIG. 7"

Using the cosmetics of Examples 28–30, the skin continuous irritation test of octylmethoxycinnamate (MCX) was conducted with the aforementioned method using marmots.

Figure 8:
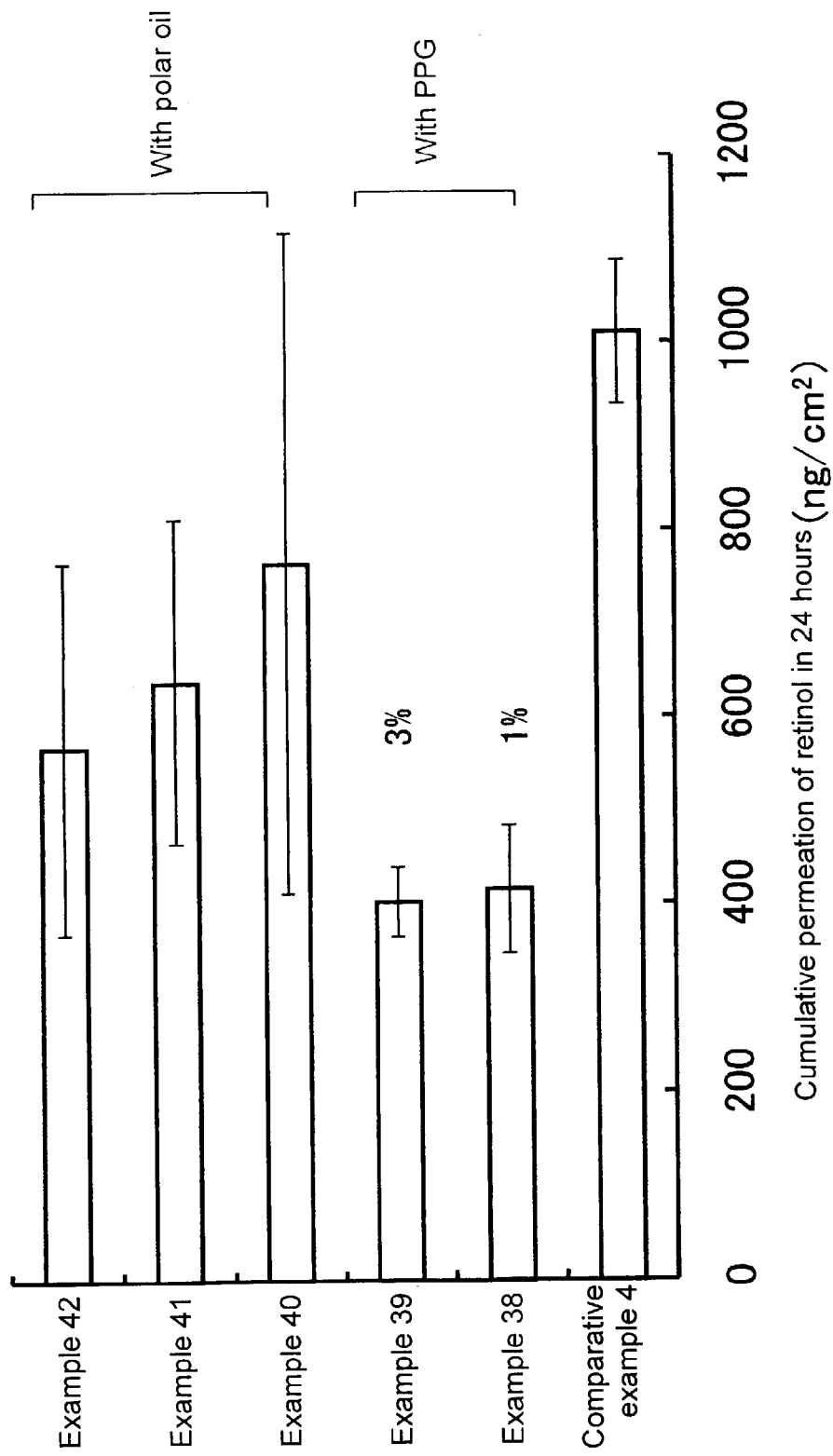
FIG. 8 is a graph showing the cumulative permeation of a lipophilic drug in 24 hours.

The results for Comparative example 1 are also shown in FIG. 8.

The cosmetics of Examples 28–30 cause less skin irritation compared with Comparative example 1 (control), and exhibit a highly superior skin irritation alleviating effect.

Examples of the present invention containing polybutylene glycol are shown below.

Each of these suppresses skin absorption of an ultraviolet absorbent and manifests an irritation alleviating effect.

Example 31

Sunscreen

| | |
|---|---|
| Octylmethoxycinnamate | 7.5 |
| Polybutylene glycol 1000 | 2.0 |
| t-Butyl methoxy dibenzoylmethane | 0.1 |
| Titanium dioxide | 5.0 |
| Decamethylcyclopentasiloxane | 30.0 |
| POE/methyl polysiloxane copolymer | 3.0 |
| Organo-modified montmorillonite | 0.8 |
| 1,3-butylene glycol | 5.0 |
| Arbutin | 5.0 |
| Preservative | Appropriate amount |
| Perfume | Appropriate amount |
| Purified water | Balance |

Example 32

Cream

| A | |
|---|---|
| Squalane | 6.0 |
| Polybutylene glycol 2000 | 4.0 |
| Petrolatum | 5.0 |
| Stearyl alcohol | 3.0 |
| Stearic acid | 3.0 |
| Glyceryl monostearate | 3.0 |
| Ethyl polyacrylate | 1.0 |
| t-Butyl methoxybenzoyl methane | 7.5 |
| Polyamide resin powder | 5.0 |
| Ethanol | 40.0 |
| Preservative | Appropriate amount |
| Perfume | Appropriate amount |

| B | |
|---|---|
| 1,3-butylene glycol | 7.0 |
| Trisodium edetate | 0.05 |
| Cationic thickener | 3.0 |
| Lactic acid | 0.6 |
| Purified water | Balance |

(Preparation method) The ingredients in A were heated and melted, to which B was added while stirring. A homogenizer was used to make the emulsion particles finer, followed by rapid cooling with stirring to obtain a cream.

Example 33

Lotion

| A | |
|---|---|
| Octylmethoxycinnamate | 2.0 |
| Tetrapentaerythrityl octanoate | 1.0 |
| Polyoxyethylene (20) oleyl alcohol ether | 0.5 |
| Ethanol | 60.0 |
| Perfume | Appropriate amount |
| Preservative | Appropriate amount |

| B | |
|---|---|
| Sorbitol | 4.0 |
| Dipropylene glycol | 6.0 |
| Polybutylene glycol 2000 | 5.0 |
| Lactic acid | 0.1 |
| Citric acid | 0.1 |
| Sodium citrate | 0.05 |
| Sodium hydroxy methoxy benzophenonesulfonate | Appropriate amount |
| Trisodium edetate | Appropriate amount |
| Purified water | Balance |

(Preparation method) B was prepared. Separately, the other ingredients of A were dissolved in ethanol to prepare A, which was added to B and dissolved and filtered to obtain a lotion.

Example 34

Latex

| A | |
|---|---|
| Stearic acid | 2.0 |
| Cetyl alcohol | 0.5 |
| Liquid paraffin | 10.0 |
| Polyoxyethylene (10) oleate | 1.0 |
| Sorbitan trioleate | 1.0 |
| Octylmethoxycinnamate | 3.0 |
| Tetrapentaerythrityl octanoate | 1.5 |
| Isopropyl myristate | 2.0 |
| Silica | 3.0 |
| Preservative | Appropriate amount |
| Perfume | Appropriate amount |

| B | |
|---|---|
| Dipropylene glycol | 5.0 |
| Polybutylene glycol 2000 | 5.0 |
| Triethanolamine | 1.0 |
| Hectorite | 1.0 |
| Citric acid | 0.2 |
| Ethanol | 55.0 |
| Purified water | Balance |

(Preparation method) B was prepared and the temperature was maintained at 70° C. The ingredients in A were mixed, heated and melted and the temperature was maintained at 70° C. A was added to B, followed by rapid cooling while a homogenizer was used for emulsification and stirring to obtain an emulsion.

Example 35

Sunblock Hair Gel

| A | |
|---|---|
| Carbopol 940 | 0.6 |
| B | |
| Purified water | 68.0 |
| C | |
| Triethanolamine | 0.1 |
| D | |
| Ethanol | 14.0 |
| Octylmethoxycinnamate | 7.5 |
| Polybutylene glycol 4800 | 4.0 |
| Methoxyethyl acrylate/hydroxyethyl acrylate/butyl acrylate copolymer | 1.0 |
| Polyethylene glycol | 1.0 |
| Dimethicone copolymer | 4.0 |
| Methylparaben | 0.25 |
| Propylparaben | 0.05 |
| Perfume | Appropriate amount |

(Preparation method) A was dissolved in B while stirring, to which C was added and dispersed with a disperser, to which D was added and stirred to obtain the target hair gel.

Example 36

Sunblock Emulsified Foundation

| A | |
|---|---|
| Purified water | 52.0 |
| 1,3-butylene glycol | 5.0 |
| Ethanol | 7.0 |
| B | |
| Talc | 7.0 |
| Titanium dioxide | 10.0 |
| Zinc oxide | 2.0 |
| Silicic acid anhydride | 2.0 |
| Nylon powder | 4.0 |
| Color pigment | 2.0 |
| C | |
| Paramethoxycinnamate | 15.0 |
| Polybutylene glycol 1000 | 4.0 |
| Octamethylcyclotetrasiloxane | 10.0 |
| Pentaerythritol rosinate | 1.5 |
| Neopentyl glycol diisooctanoate | 5.0 |
| Glycerin triisooctanoate | 2.0 |
| Polyoxyethylene modified dimethylpolysiloxane | 1.5 |
| Trimethylsiloxy silicic acid resin | 5.0 |

(Preparation method) After stirring A, thoroughly mixed and crushed B was added, follow by a homogenizer treatment. C was dissolved and added to this, followed by a homogenizer treatment to obtain a sunblock emulsified foundation.

"Sensitization Suppression Test"

Next, a cosmetic containing polypropylene glycol (PPG) and octyl methoxycinnamate (MCX) and a cosmetic containing polybutylene glycol (PBG) and octylmethoxycinnamate were tested for the sensitization suppression effect of MCX with the Maximization Test (MAX method) described below.

Example 37 is a cosmetic similar to Example 1 except for the fact that 2 mass % PBG1000, instead of PPG200, was blended in.

Example 30 is a cosmetic similar to Example 1 except for the fact that 2 mass % PBG1000, instead of PPG200, was blended in.

Comparative example 3 is a cosmetic similar to Comparative example 1 except for the fact that octylmethoxycinnamate was removed.

The results are shown in Table 3.

These results indicate that both PPG and PBG have a superior sensitization suppression effect on MCX.

"MAX Method" (Marmot Skin Contact Sensitization Test)

A group of five 7–10 week old healthy Hartley strain marmots were used to conduct Manusson and Kligman's GPMT method (guinea pig maximization test, 1970 Allergic contact dermatitis in the guinea pig. Springfield. Ill. C. C. Thomas).

For the sensitization treatment, endodermic injections were made into the left and right shoulders of a marmot, for a total of six places, in the following order of ①~③.

① Water emulsion (FCA : $H_2O$=1:1, V/V) of 0.1 mL Freund's complete adjuvant: (hereafter abbreviated as FCA; from Difco), ② 0.1 mL sample solution (5, 7.5, 10% MCX liquid petrolatum solution)

③ A mixture of a MCX liquid petrolatum solution having a concentration twice as much as ② and FCA.

After seven days, 0.2 mL of the sample solution (5, 7.5, 10% MCX liquid petrolatum solution) was applied with 48 hour occlusion on the injection site(s) where a small amount of 10 W/V% laurylsulfate soda/white petrolatum was applied after shaving the day before.

The induction test was performed two weeks after the aforementioned procedure by applying 10 microliters of the sample solution (the sample solution listed in Table 3) on the back and abdominal skin with 24 hour open conditions.

As a control for each test, the same number of animals which received endodermic injections of only the water emulsion of FCA were used to distinguish a non-specific skin irritation reaction.

Evaluation was done based on the following evaluation criteria 48 hours after the application.

"Evaluation Criteria"

| (1) Formation of erythema and scabs | Score |
|---|---|
| No erythema is observed. | 0 |
| Slight erythema is observed. | 1 |
| Prominent erythema is observed. | 2 |
| Severe erythema is observed. | 3 |
| Severe erythema accompanied by scabs is observed. | 4 |

| (2) Formation of edema | Score |
|---|---|
| No edema is observed. | 0 |
| Slight edema is observed. | 1 |

-continued

| (2) Formation of edema | Score |
|---|---|
| Prominent edema is observed. | 2 |
| Severe edema is observed. | 3 |

The sensitization rate and score are determined as follows.

Sensitization rate=Number of animals that exhibited skin reactions/Number of animals that received the sensitization treatment Score=Σ (Erythema score+Edema score)/Number of animals that received the sensitization treatment

TABLE 3

| | MAX method | | | | | |
|---|---|---|---|---|---|---|
| | 10% MCX Sensitization | | 7.5% MCX Sensitization | | 5% MCX Sensitization | |
| Sensitization method Sample solution | Sensitization ratio | Average score | Sensitization ratio | Average score | Sensitization ratio | Average score |
| Comparative example 1 | 3/5 | 0.6 | 4/5 | 1.0 | 5/5 | 1.6 |
| Example 37(PPG-1000 2%) | 1/5 | 0.2 | 3/5 | 0.6 | 3/5 | 1.0 |
| Example 30(PBG-1000 2%) | — | — | 2/5 | 0.4 | 2/5 | 0.8 |
| Comparative example 3 | 0/5 | 0.0 | 0/5 | 0.0 | 0/5 | 0.0 |

The numeric values indicate (2) Invention of Claims 11–18

An endermic liniment containing retinol (all-trans type) for the lipophilic drug was prepared with a conventional method.

Examples 38–39 have polypropylene glycol for the irritation alleviating agent.

Examples 40–42 have a polar oil for the irritation alleviating agent.

Comparative example 4 is a control.

Comparative example 4 does not have the irritation alleviating agent of the present invention.

Using the endermic liniments of Examples 38–42 and Comparative example 4, the skin absorption test and the continuous skin irritation test were conducted for the aforementioned lipophilic drug.

"Description of FIG. 8"

Using the endermic liniments of Examples 38–42 and Comparative example 4, a skin absorption test for retinol was conducted with the aforementioned method by using lab-skin.

The results are shown in FIG. 8.

The endermic liniments of Examples 38–42 are superior to Comparative example 4 (control) in terms of the skin absorption suppression effect.

In particular, the results of Example 38 and Example 39 indicate a very superior skin absorption suppression effect for polypropylene glycol.

Figure 9:
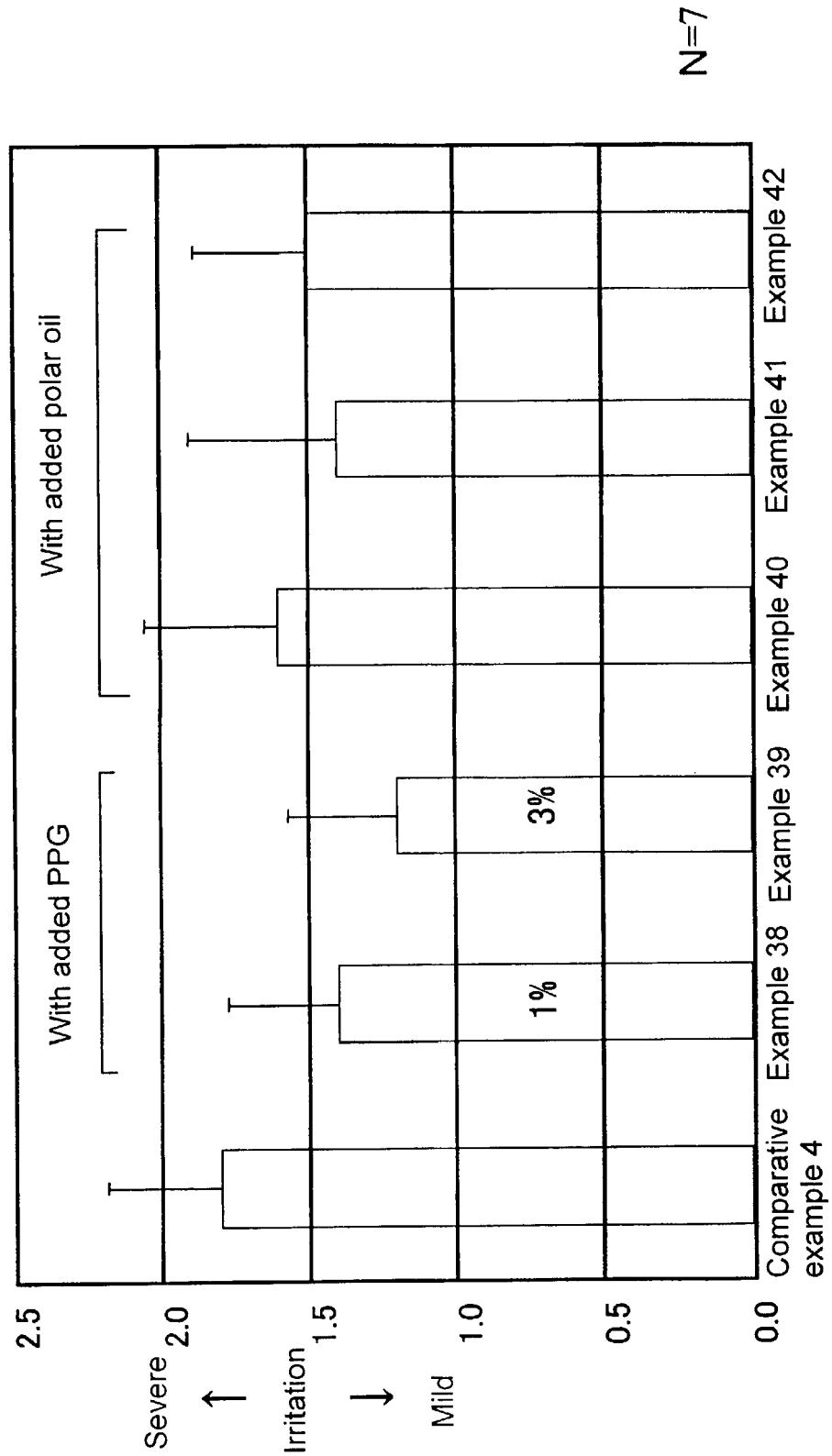
FIG. 9 is a graph showing the continuous skin irritation test results of a lipophilic drug.

"Description of FIG. 9"

Using the endermic liniments of Examples 38–42 and Comparative example 4, a skin continuous irritation test for

TABLE 4

| | Blend ratios are in mass % units. | | | | | |
|---|---|---|---|---|---|---|
| Raw material name | Comparative example 4 control | Example 38 PPG3000 1% | Example 39 PPG3000 3% | Example 40 Pentaerythrityl tetraoctanoate 3% | Example 41 Pentaerythrityl tetraoctanoate 8% | Example 42 Cetyl octanoate 8% |
| Purified water | Balance | Balance | Balance | Balance | Balance | Balance |
| EDTA-3Na.2H$_2$O | 0.01 | 0.01 | 0.01 | 0.01 | 0.01 | 0.01 |
| Dipropylene glycol | 5 | 5 | 5 | 5 | 5 | 5 |
| Purified water | 29.7 | 29.7 | 29.7 | 29.7 | 29.7 | 29.7 |
| Carboxyvinyl polymer | 0.3 | 0.3 | 0.3 | 0.3 | 0.3 | 0.3 |
| Brucine-modified alcohol | 2 | 2 | 2 | 2 | 2 | 2 |
| POE glyceryl isostearate | 1.1 | 1.1 | 1.1 | 1.1 | 1.1 | 1.1 |
| POE glycerin monostearate | 0.9 | 0.9 | 0.9 | 0.9 | 0.9 | 0.9 |
| Behenyl alcohol | 0.6 | 0.6 | 0.6 | 0.6 | 0.6 | 0.6 |
| Batyl alcohol | 0.6 | 0.6 | 0.6 | 0.6 | 0.6 | 0.6 |
| Methyl polysiloxane | 3 | 3 | 3 | 3 | 3 | 3 |
| Squalane | 8 | 7 | 5 | 5 | 0 | 0 |
| Pentaerythrityl tetraoctanoate | 0 | 0 | 0 | 3 | 8 | 0 |
| Cetyl octanoate | 0 | 0 | 0 | 0 | 0 | 8 |
| Polypropylene glycol | 0 | 1 | 3 | 0 | 0 | 0 |
| Dibutylhydoxytoluene | 0.05 | 0.05 | 0.05 | 0.05 | 0.05 | 0.05 |
| Ethylparaben | 0.12 | 0.12 | 0.12 | 0.12 | 0.12 | 0.12 |
| Butylparaben | 0.1 | 0.1 | 0.1 | 0.1 | 0.1 | 0.1 |
| Retinol | 0.2 | 0.2 | 0.2 | 0.2 | 0.2 | 0.2 |
| Potassium hydroxide | 0.11 | 0.11 | 0.11 | 0.11 | 0.11 | 0.11 |
| Glycerin | 10 | 10 | 10 | 10 | 10 | 10 | retinol was conducted with the aforementioned method by using marmots.

The endermic liniments of Examples 38–42 exhibit lower skin irritation compared with Comparative example 4 (control).

In particular, the results of Example 38 and Example 39 exhibit a very superior skin irritation suppression effect of polypropylene glycol.

As for the polar oil, a superior skin irritation suppression effect is obtained when the blend ratio of pentaerythrityl tetraoctanoate is 8 mass %.

When determining ingredients of an endermic liniment, the cost, usability, and formulation design feasibility are important factors.

From this point of view, polypropylene glycol and, among polar oils, cetyl octanoate are preferable.

Figure 10:
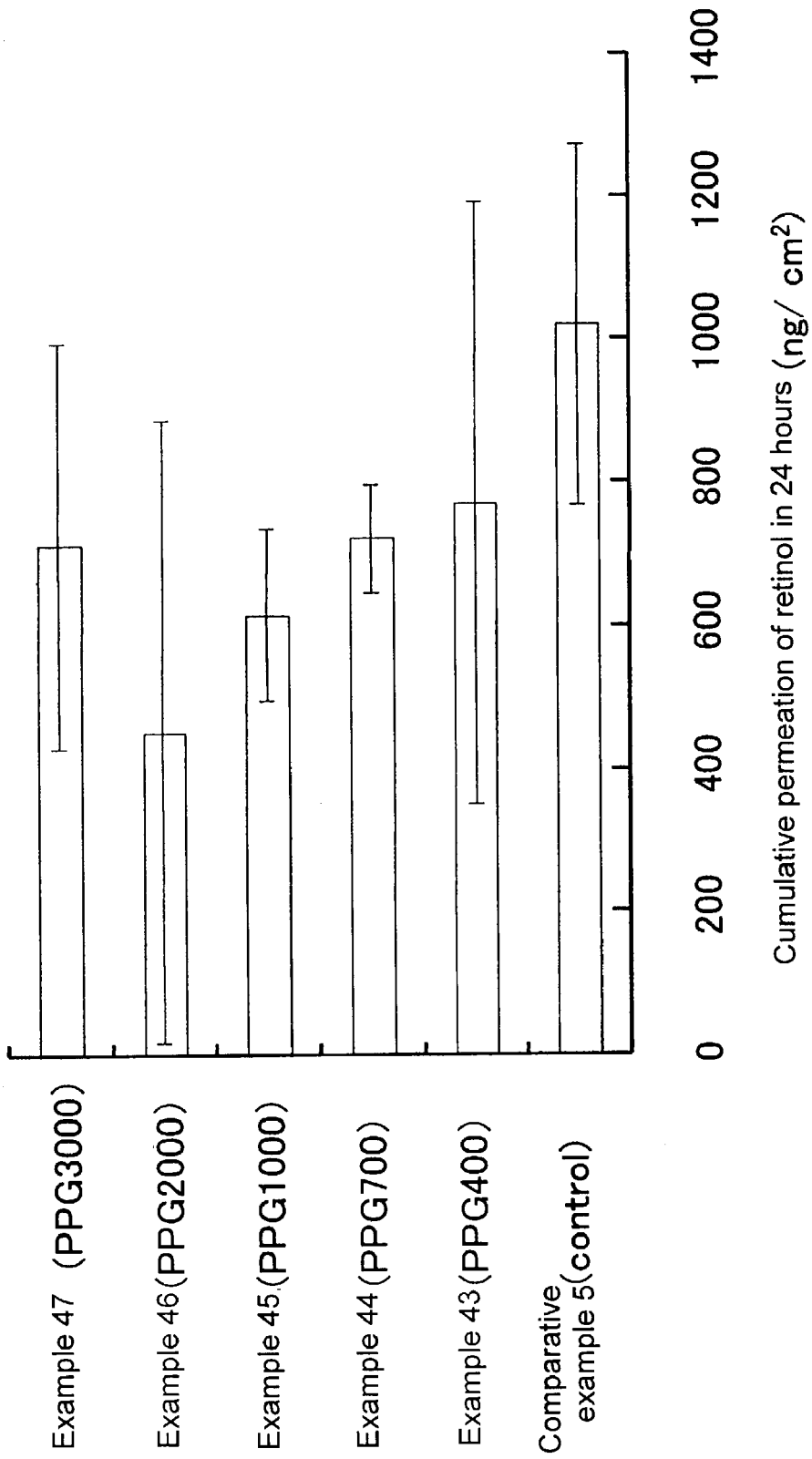
FIG. 10 is a graph showing the cumulative permeation of a lipophilic drug in 24 hours.

The results shown in FIG. 8 and FIG. 9 indicate that there is a correlation between the skin absorption suppression effect and the skin irritation alleviating effect.

with a conventional method, and the aforementioned skin absorption suppression test was conducted. The results are shown in FIG. 10.

The endermic liniments of Examples 43–47 are superior to Comparative example 5 (control) in terms of the skin absorption suppression effect.

In particular, the result of Example 46 indicates that polypropylene glycol 2000 specifically has a very superior skin absorption suppression effect.

From this result, polypropylene glycol having a molecular weight of 1,500–2,500 is expected to have a particularly superior skin absorption suppression effect.

It is believed that there is a correlation between the skin absorption suppression effect and the skin irritation alleviating effect. Polypropylene glycol therefore is estimated to have a specifically high skin irritation alleviating effect when the molecular weight is around 2,000, i.e. 1,500–2,500.

TABLE 5

Blend ratios are in mass % units.

| Raw material name | Comparative example 5 control | Example 43 PPG400 | Example 44 PPG700 | Example 45 PPG1000 | Example 46 PPG2000 | Example 47 PPG3000 |
|---|---|---|---|---|---|---|
| Purified water | Balance | Balance | Balance | Balance | Balance | Balance |
| EDTA-3Na·2H$_2$O | 0.01 | 0.01 | 0.01 | 0.01 | 0.01 | 0.01 |
| Dipropylene glycol | 5 | 5 | 5 | 5 | 5 | 5 |
| Purified water | 29.7 | 29.7 | 29.7 | 29.7 | 29.7 | 29.7 |
| Carboxyvinyl polymer | 0.3 | 0.3 | 0.3 | 0.3 | 0.3 | 0.3 |
| Brucine-modified alcohol | 2 | 2 | 2 | 2 | 2 | 2 |
| POE glyceryl isostearate | 1.1 | 1.1 | 1.1 | 1.1 | 1.1 | 1.1 |
| POE glycerin | 0.9 | 0.9 | 0.9 | 0.9 | 0.9 | 0.9 |
| Behenyl alcohol | 0.6 | 0.6 | 0.6 | 0.6 | 0.6 | 0.6 |
| Batyl alcohol | 0.6 | 0.6 | 0.6 | 0.6 | 0.6 | 0.6 |
| Squalane | 8 | 7 | 7 | 7 | 7 | 7 |
| Polypropylene glycol 400 | 0 | 1 | 0 | 0 | 0 | 0 |
| Polypropylene glycol 700 | 0 | 0 | 1 | 0 | 0 | 0 |
| Polypropylene glycol 1000 | 0 | 0 | 0 | 1 | 0 | 0 |
| Polypropylene glycol 2000 | 0 | 0 | 0 | 0 | 1 | 0 |
| Polypropylene glycol 3000 | 0 | 0 | 0 | 0 | 0 | 1 |
| Dibutylhydoxytoluene | 0.05 | 0.05 | 0.05 | 0.05 | 0.05 | 0.05 |
| Ethylparaben | 0.12 | 0.12 | 0.12 | 0.12 | 0.12 | 0.12 |
| Butylparaben | 0.1 | 0.1 | 0.1 | 0.1 | 0.1 | 0.1 |
| Retinol | 0.1668 | 0.1668 | 0.1668 | 0.1668 | 0.1668 | 0.1668 |
| Potassium hydroxide | 0.11 | 0.11 | 0.11 | 0.11 | 0.11 | 0.11 |
| Glycerin | 10 | 10 | 10 | 10 | 10 | 10 |

"Description of FIG. 10"

Example 38 and Example 39 indicate that polypropylene glycol has a superior skin absorption suppression effect and skin irritation alleviating effect.

The relationship between the molecular weight of polypropylene glycol and the skin absorption suppression effect was investigated.

Figure 11:
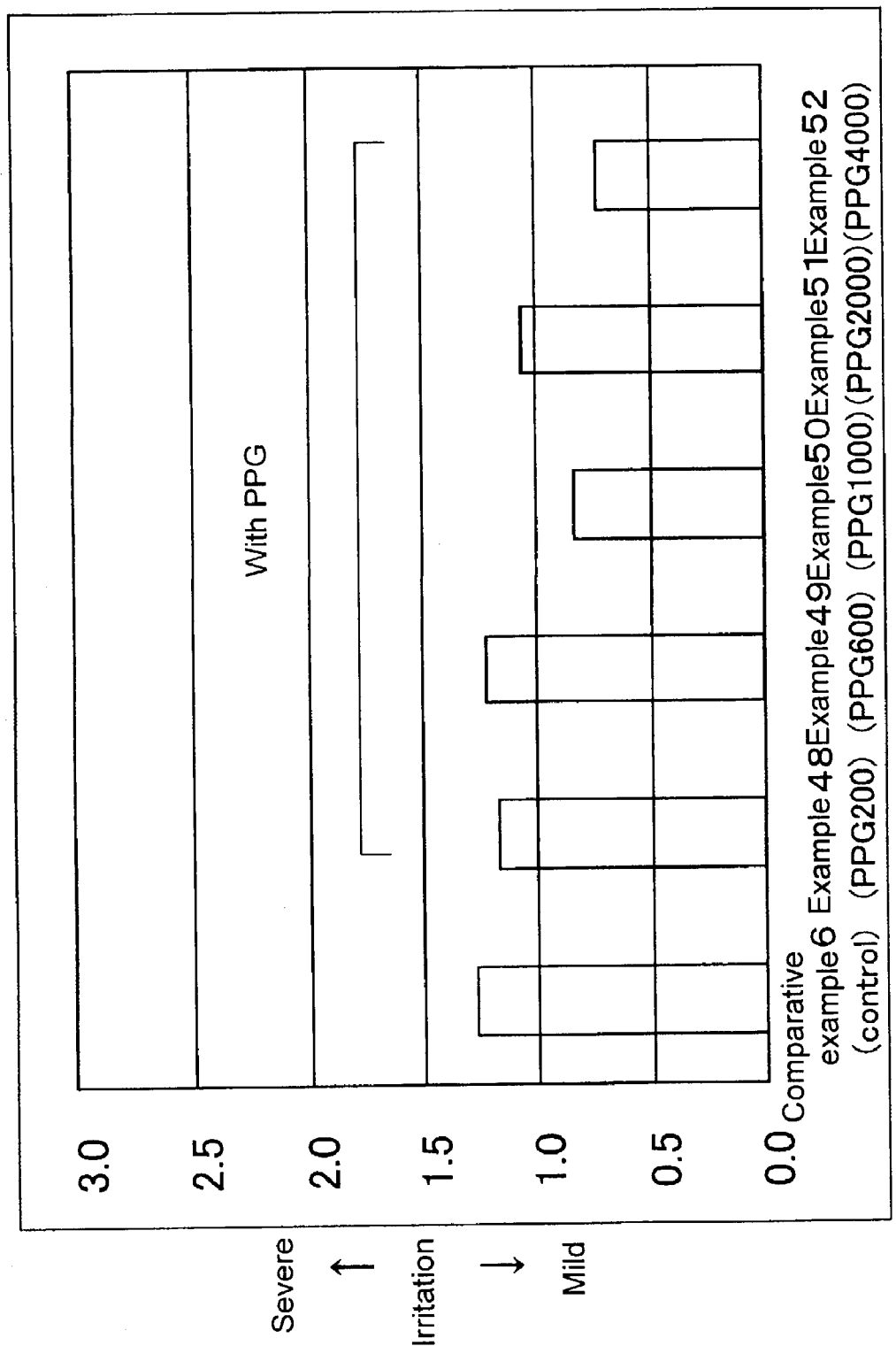
FIG. 11 is a graph showing the continuous skin irritation test results of a lipophilic drug.

Using recipes listed in Table 5, endermic liniments of Examples 43–47 and Comparative example 5 were prepared "Description of FIG. 11"

Using an endermic liniment containing octylmethoxycinnamate for the lipophilic drug (listed in Table 6), the continuous skin irritation test for PPG (irritation alleviating agent) was conducted.

The result is shown in FIG. 11.

This result indicates that the irritation alleviating effect of PPG against octylmethoxycinnamate is superior when the number average molecular weight of the PPG is around 1,000 and 4,000.

TABLE 6

Blend ratios are in mass % units.

| Raw material name | Comparative example 6 control | Example 48 PPG200 | Example 49 PPG600 | Example 50 PPG1000 | Example 51 PPG2000 | Example 52 PPG4000 |
|---|---|---|---|---|---|---|
| Purified water | Balance | Balance | Balance | Balance | Balance | Balance |
| PPG-200 | — | 3 | — | — | — | — |
| PPG-600 | — | — | 3 | — | — | — |
| PPG-1000 | — | — | — | 3 | — | — |
| PPG-2000 | — | — | — | — | 3 | — |
| PPG-4000 | — | — | — | — | — | 3 |
| 1,3-butylene glycol | 5 | 5 | 5 | 5 | 5 | 5 |
| POE/methyl polysiloxane copolymer | 2 | 2 | 2 | 2 | 2 | 2 |
| Clay mineral (Hectorite) | 0.5 | 0.5 | 0.5 | 0.5 | 0.5 | 0.5 |
| Decamethylcyclopentasiloxane | 30 | 30 | 30 | 30 | 30 | 30 |
| Trimethylsiloxysilicic acid-Decamethylcyclopentasiloxane solution | 5 | 5 | 5 | 5 | 5 | 5 |
| Methyl polysiloxane | 5 | 5 | 5 | 5 | 5 | 5 |
| Octyl methoxycinnamate | 7.5 | 7.5 | 7.5 | 7.5 | 7.5 | 7.5 |
| Fine particle zinc oxide | 20 | 20 | 20 | 20 | 20 | 20 |
| Methyl polymethacrylate | 4 | 4 | 4 | 4 | 4 | 4 |
| EDTA-3Na.2H$_2$O | 0.05 | 0.05 | 0.05 | 0.05 | 0.05 | 0.05 |
| Methylparaben | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount |
| Total | 100 | 100 | 100 | 100 | 100 | 100 |

Recipe example of endermic liniments containing the irritation alleviating agent of the present invention are shown below.

Example 53

| Lipstick | (mass %) |
|---|---|
| Solid paraffin | 8.0 |
| Carnauba wax | 2.0 |
| Candelilla wax | 4.0 |
| Microcrystalline wax | 6.0 |
| Hydrogenated lanolin | 15.0 |
| Glyceryl diisostearate | 30.0 |
| PEG1000 | 15.0 |
| PPG2000 | 1.0 |
| Retinol | 1.0 |
| BHT | 0.3 |
| Blended coloring agent (red-type) | 7.0 |
| Perfume | Appropriate amount |
| Isopropyl palmitate | Balance |

Example 54

| Lotion | (mass %) |
|---|---|
| Retinol | 0.0001 |
| Oleyl alcohol | 0.001 |
| α-tocopherol | 0.005 |
| POE (20) octyl dodecanol | 0.8 |
| Ethanol | 8.0 |
| PPG1500 | 1.0 |
| Methylparaben | 0.15 |
| Lactic acid | 0.03 |
| Sodium lactate | 0.07 |
| Purified water | Balance |

Example 55

| Eye wrinkle oil | (mass %) |
|---|---|
| Olive oil | 40.0 |
| Triglyceride 2-ethylhexanoate | 26.0 |
| Squalane | 30.0 |
| PPG1000 | 2.0 |
| δ-tocopherol | 1.0 |
| Retinol | 0.1 |

Example 56

| Night cream | (mass %) |
|---|---|
| Squalane | 15.0 |
| Isopropyl myristate | 5.0 |
| Silicon dioxide | 3.0 |
| Petrolatum | 6.0 |
| Glyceryl monoiso stearate | 2.0 |
| POE (7) hydrogenated castor oil | 1.5 |
| Propylparaben | 0.2 |
| Retinol | 0.4 |
| Pentaerythrityl tetraoctanoate | 6.0 |
| Glycerin | 17.0 |
| Purified water | Balance |

Example 57

| Emulsion | (mass %) |
| --- | --- |
| A. | |
| Squalane | 5.0 |
| Oleyl oleate | 3.0 |
| Glycerin | 2.0 |
| Sorbitan sesquioleic ester | 0.8 |
| Polyoxyethylene oleyl ether (20 EO) | 1.2 |
| Retinol | 0.1 |
| Cetyl octanoate | 0.5 |
| Perfume | 0.3 |
| Preservative | Appropriate amount |
| B. | |
| 1,3 butylene glycol | 4.5 |
| Ethanol | 3.0 |
| Carboxyvinyl polymer | 0.2 |
| Potassium hydroxide | 0.1 |
| L-arginine L-aspartate | 0.01 |
| Turmeric extract (dry weight) | 0.001 |
| Sodium hexametaphosphate | 0.05 |
| Purified water | Balance |

Example 58

| Eye cream | (mass %) |
| --- | --- |
| Glycerin | 14.0 |
| Carboxyvinyl polymer | 0.1 |
| Polyoxybehenyl ether | 1.0 |
| Behenyl alcohol | 4.0 |
| Stearyl alcohol | 2.0 |
| Petrolatum | 5.0 |
| Pentaerythrityl tetraoctanoate | 12.0 |
| Dimethicone | 5.0 |
| Retinol acetate | 0.17 |
| Tocopheryl acetate | 0.5 |
| Evening primrose oil | 0.2 |
| Hyaluronic acid | 0.1 |
| MPC copolymer | 3.0 |
| Tormentilla root extract | 0.1 |
| Magnesium ascorbate phosphate | 0.1 |
| Hydrolyzed eggshell membrane | 0.1 |
| Silica | 3.0 |
| Edetate | 0.1 |
| Paraben | 0.2 |
| Perfume | 0.03 |
| Ion-exchange water | Balance |

Next, the skin absorption test and continuous skin irritation test were conducted for polybutylene glycol (PBG) in the same manner as described above.

Example 59 is an endermic liniment similar to Example 38 except for the fact that 1 mass % PBG4800, instead of PPG3000, was blended in.

Example 60 is an endermic liniment similar to Example 38 except for the fact that 1 mass % PBG200, instead of PPG3000, was blended in.

Example 61 is an endermic liniment similar to Example 38 except for the fact that 1 mass % PBG1000, instead of PPG3000, was blended in.

Example 62 is an endermic liniment similar to Example 48 except for the fact that 2 mass % PBG4800, instead of PPG200, was blended in.

Example 63 is an endermic liniment similar to Example 48 except for the fact that 2 mass % PBG2000, instead of PPG200, was blended in.

Example 64 is an endermic liniment similar to Example 48 except for the fact that 2 mass % PBG1000, instead of PPG200, was blended in.

The results of the skin absorption test and the continuous skin irritation test for the aforementioned endermic liniments of Examples 59–64 are shown in FIGS. 12–15.

Figure 12:
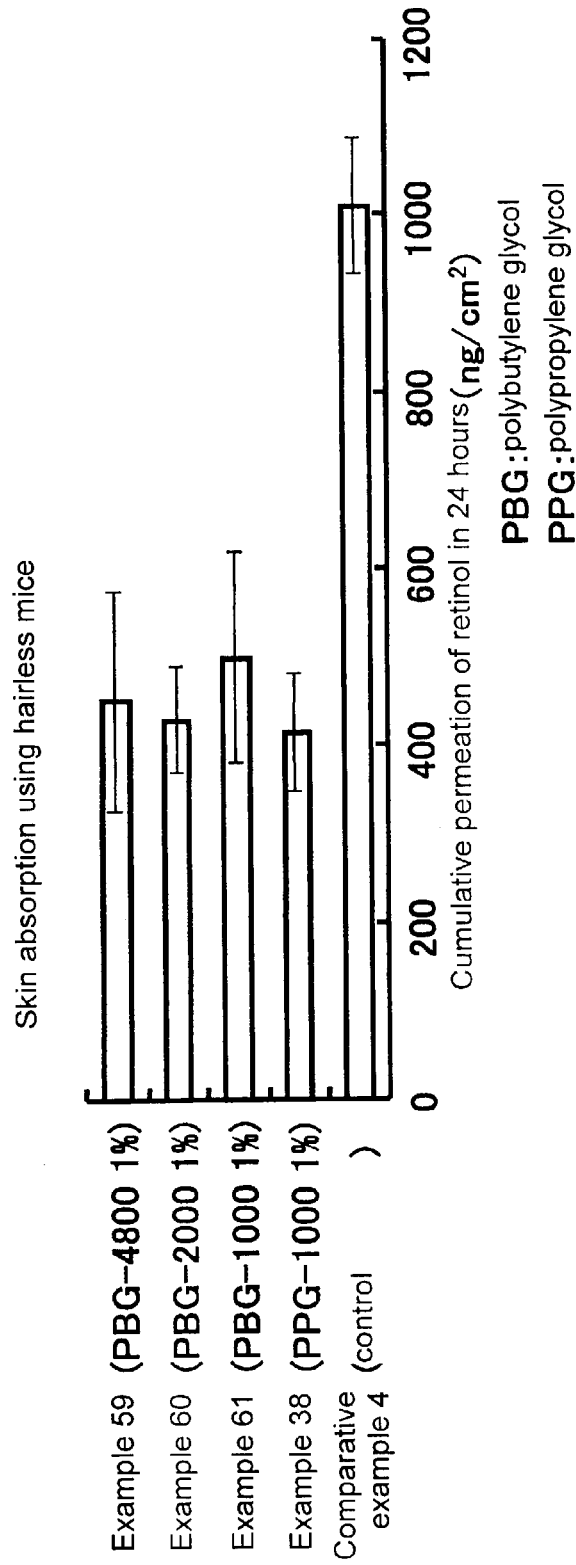
FIG. 12 is a graph showing the cumulative permeation of a lipophilic drug in 24 hours.

"Description of FIG. 12"

Using the endermic liniments of Examples 59–61, the skin absorption test of retinol was conducted with the aforementioned method using hairless mouse skin.

The results for Example 38 and Comparative example 4 are also shown in FIG. 12.

The endermic liniments of Examples 59–61 have a superior skin absorption suppression effect compared with Comparative example 1 (control).

The PBG of Examples 59–61 has a superior skin absorption suppression effect comparable to that of the PPG of Example 38.

Figure 13:
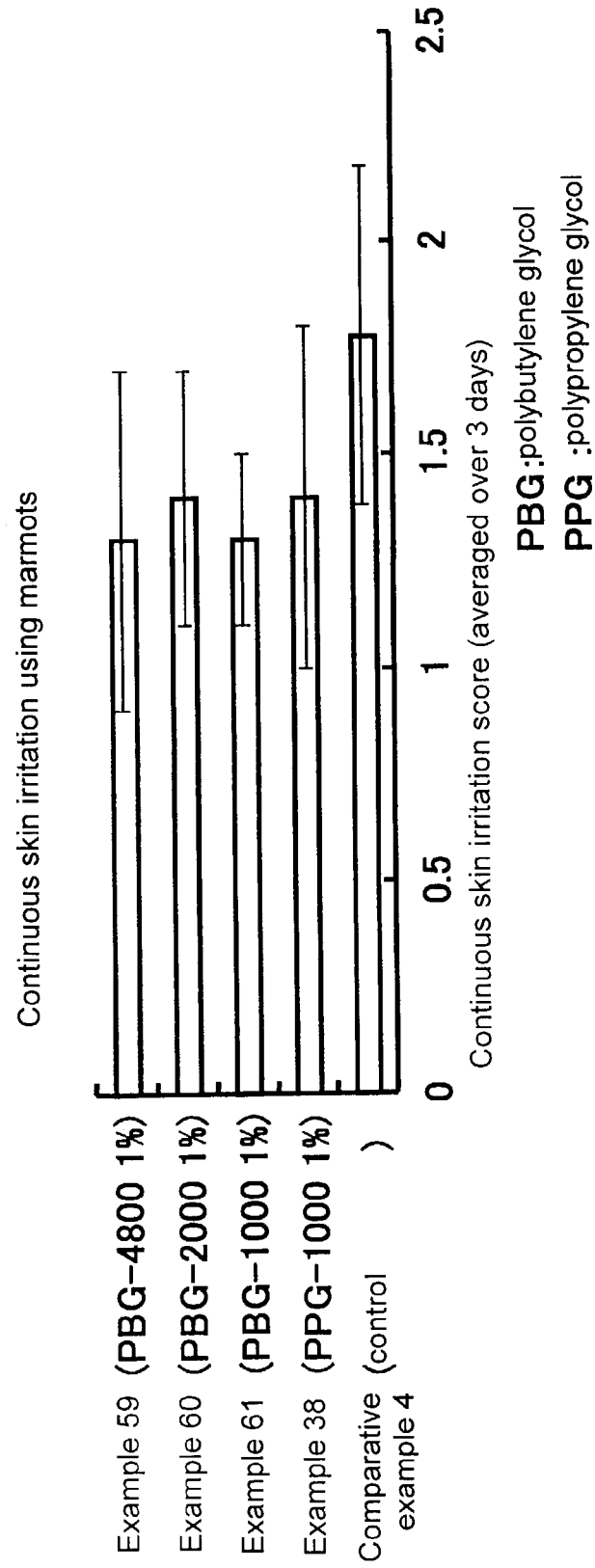
FIG. 13 is a graph showing the continuous skin irritation test results of a lipophilic drug.

"Description of FIG. 13"

Using the endermic liniments of Examples 59–61, the skin continuous irritation test of retinol was conducted with the aforementioned method using marmots.

The results for Example 38 and Comparative example 4 are also shown in FIG. 12.

The endermic liniments of Examples 59–61 cause less skin irritation compared with Comparative example 4 (control).

In particular, they have a superior skin irritation alleviating effect comparable to or even better than the PPG of Example 38.

Figure 14:
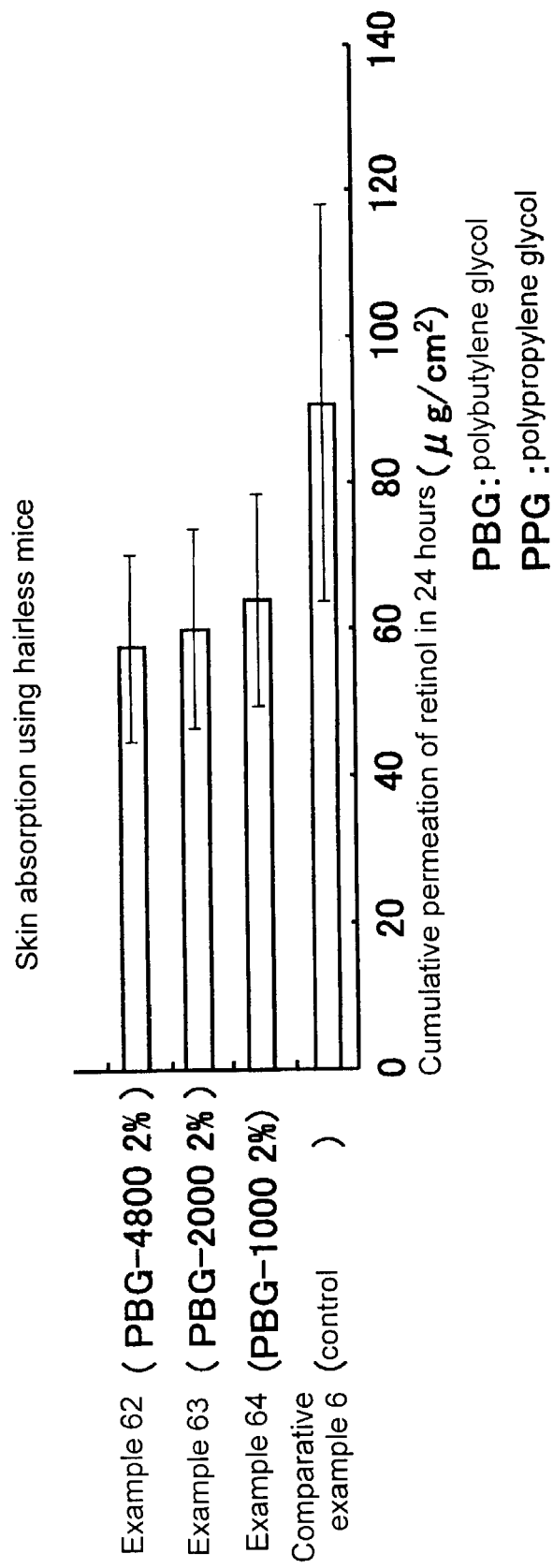
FIG. 14 is a graph showing the cumulative permeation of a lipophilic drug in 24 hours.

"Description of FIG. 14"

Using the endermic liniments of Examples 62–64, the skin absorption test of octylmethoxycinnamate (MCX) was conducted with the aforementioned method using hairless mouse skin.

The results for Comparative example 6 are also shown in FIG. 14.

The endermic liniments of Examples 62–64 have a superior skin absorption suppression effect compared with Comparative example 6 (control).

Figure 15:
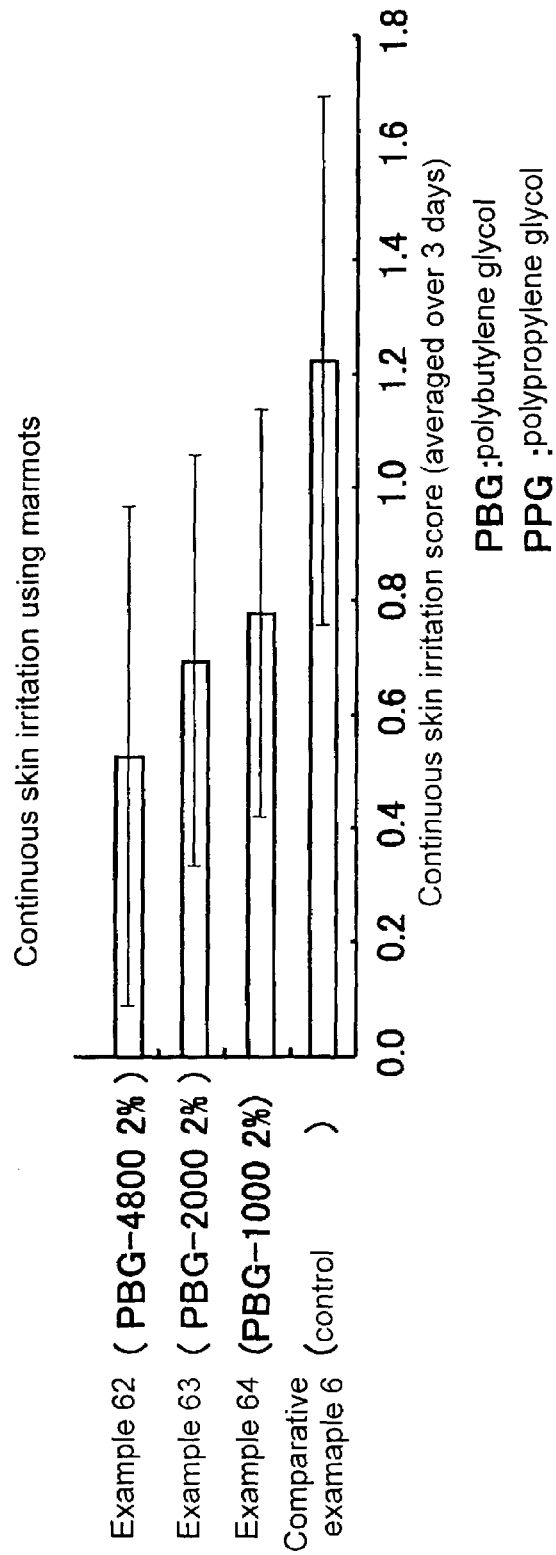
FIG. 15 is a graph showing the continuous skin irritation test results of a lipophilic drug.

"Description of FIG. 15"

Using the endermic liniments of Examples 62–64, the skin continuous irritation test of octylmethoxycinnamate (MCX) was conducted with the aforementioned method using marmots.

The results for Comparative example 6 are also shown in FIG. 15.

The endermic liniments of Examples 62–64 cause less skin irritation compared with Comparative example 1 (control), and exhibit a highly superior skin irritation alleviating effect.

Examples of endermic liniment recipes having polybutylene glycol for the irritation alleviating agent are shown below.

Example 65

| Lipstick | (mass %) |
| --- | --- |
| Solid paraffin | 8.0 |
| Carnauba wax | 2.0 |
| Candelilla wax | 4.0 |

-continued

| Lipstick | (mass %) |
|---|---|
| Microcrystalline wax | 6.0 |
| Lanolin hydrate | 15.0 |
| Glyceryl diisostearate | 30.0 |
| PEG1000 | 15.0 |
| PBG2000 | 1.0 |
| Retinol | 1.0 |
| BHT | 0.3 |
| Blended coloring agent (red-type) | 7.0 |
| Perfume | Appropriate amount |
| Isopropyl palmitate | Balance |

Example 66

| Lotion | (mass %) |
|---|---|
| Retinol | 0.0001 |
| Oleyl alcohol | 0.001 |
| α-Tocopherol | 0.005 |
| POE (20) octyl dodecanol | 0.8 |
| Ethanol | 8.0 |
| PBG1000 | 1.0 |
| Methylparaben | 0.15 |
| Lactic acid | 0.03 |
| Sodium lactate | 0.07 |
| Purified water | Balance |

Example 67

| Eye wrinkle oil | (mass %) |
|---|---|
| Olive oil | 40.0 |
| Triglyceride 2-ethylhexanoate | 26.0 |
| Squalane | 30.0 |
| PBG1000 | 2.0 |
| δ-tocopherol | 1.0 |
| Retinol | 0.1 |

Example 68

| Night cream | (mass %) |
|---|---|
| Squalane | 15.0 |
| Isopropyl myristate | 5.0 |
| Silicon dioxide | 3.0 |
| Petrolatum | 6.0 |
| Glyceryl monoiso stearate | 2.0 |
| POE (7) hydrogenated castor oil | 1.5 |
| Propylparaben | 0.2 |
| Retinol | 0.4 |
| PBG4800 | 6.0 |
| Glycerin | 17.0 |
| Purified water | Balance |

Example 69

| Emulsion | (mass %) |
|---|---|
| A. | |
| Squalane | 5.0 |
| Oleyl oleate | 3.0 |
| Glycerin | 2.0 |
| Sorbitan sesquioleic ester | 0.8 |
| Polyoxyethylene oleyl ether (20EO) | 1.2 |
| Retinol | 0.1 |
| PBG4800 | 0.5 |
| Perfume | 0.3 |
| Preservative | Appropriate amount |
| B. | |
| 1,3 Butylene glycol | 4.5 |
| Ethanol | 3.0 |
| Carboxyvinyl polymer | 0.2 |
| Potassium hydroxide | 0.1 |
| L-arginine L-aspartate | 0.01 |
| Turmeric extract (dry weight) | 0.001 |
| Sodium hexametaphosphate | 0.05 |
| Purified water | Balance |

Example 70

| Eye cream | (mass %) |
|---|---|
| Glycerin | 14.0 |
| Carboxyvinyl polymer | 0.1 |
| Polyoxybehenyl ether | 1.0 |
| Behenyl alcohol | 4.0 |
| Stearyl alcohol | 2.0 |
| Petrolatum | 5.0 |
| PBG4800 | 6.0 |
| Dimethicone | 5.0 |
| Retinol acetate | 0.17 |
| Tocopheryl acetate | 0.5 |
| Evening primrose oil | 0.2 |
| Hyaluronic acid | 0.1 |
| MPC copolymer | 3.0 |
| tormentilla root extract | 0.1 |
| Magnesium ascorbate phosphate | 0.1 |
| Hydrolyzed eggshell membrane | 0.1 |
| Silica | 3.0 |
| Edetate | 0.1 |
| Paraben | 0.2 |
| Perfume | 0.03 |
| Ion-exchange water | Balance |

INDUSTRIAL APPLICABILITY

Ultraviolet absorbents and lipophilic drugs in cosmetics may cause skin irritation. The cosmetics of the present invention are superior in terms of the skin absorption suppression effect and skin irritation alleviating effect on ultraviolet absorbents and lipophilic drugs.

Also, since the sunblock cosmetic of the present invention prevents skin absorption of the ultraviolet absorbent, it is superior in terms of ultraviolet prevention and safety. It also has a superior sensitization suppression effect for ultraviolet absorbents.

The irritation alleviating agent of the present invention has advantages in that it is inexpensive, exhibits good usability, and allows easy cosmetic formulation design.

The invention claimed is:

1. A cosmetic comprising:
   octyl methoxycinnamate; and
   at least one polar oil selected from the group consisting of diethyl sebacate, isononyl isononanoate, isooctyl succinate, trioctanoin, pentaerythrityl tetraoctanoate, and cetyl octanoate.

2. The cosmetic claim 1, or wherein said cosmetic is a sunblock cosmetic.

3. A cosmetic comprising:
   octyl methoxycinnamate; and
   polybutylene glycol having a number average molecular weight of 1000 to 4800.

4. The cosmetic of claim 3, wherein said cosmetic is a sunblock cosmetic.

5. A method of suppressing skin absorption of octyl methoxycinnamate when placed on the skin of a user comprising applying to the skin the cosmetic of claim 3.

6. A method of suppressing skin absorption of octyl methoxycinnamate when placed on the skin of a user comprising applying to the skin the cosmetic of claim 1.

* * * * *